United States Patent [19]

Farina et al.

[11] 4,378,428

[45] Mar. 29, 1983

[54] METHOD FOR CARRYING OUT NON-ISOTOPIC IMMUNOASSAYS, LABELED ANALYTES AND KITS FOR USE IN SUCH ASSAYS

[75] Inventors: Peter R. Farina, North Salem; James R. Golke, Yorktown Heights, both of N.Y.

[73] Assignee: Baker Instruments Corporation, Bethlehem, Pa.

[21] Appl. No.: 248,689

[22] Filed: Mar. 30, 1981

[51] Int. Cl.$^3$ .................. G01N 33/54; C12N 9/96
[52] U.S. Cl. ........................ 435/7; 435/188; 435/810; 436/500; 436/518; 436/528; 436/532; 436/536; 436/544; 260/112 R
[58] Field of Search ............... 435/4, 7, 18, 23, 24, 435/188, 199, 805, 810; 260/112, 121; 23/230 B; 424/8, 12

[56] References Cited

U.S. PATENT DOCUMENTS

| | | | |
|---|---|---|---|
| 3,817,837 | 6/1974 | Rubenstein et al. | 435/7 |
| 3,843,696 | 10/1974 | Wagner et al. | 260/112 R |
| 3,852,157 | 12/1974 | Rubenstein et al. | 435/188 |
| 3,856,469 | 12/1974 | Schneider et al. | 23/230 B |
| 3,875,011 | 4/1975 | Rubenstein et al. | 435/7 |
| 3,884,898 | 5/1975 | Schneider | 260/121 |
| 3,888,866 | 6/1975 | Leute et al. | 23/230 B |
| 3,905,871 | 9/1975 | Rubenstein et al. | 435/7 |
| 3,917,582 | 11/1975 | Soffer et al. | 260/112 R |
| 3,935,074 | 1/1976 | Rubenstein et al. | 435/7 |
| 3,966,556 | 6/1976 | Rubenstein et al. | 435/7 |
| 3,996,345 | 12/1976 | Ullman et al. | 424/12 |
| 3,998,943 | 12/1976 | Ullman | 424/12 |
| 4,002,532 | 1/1977 | Weltman et al. | 435/7 |
| 4,025,501 | 5/1977 | Leute | 260/121 |
| 4,039,385 | 8/1977 | Ullman et al. | 435/188 |
| 4,040,907 | 8/1977 | Ullman et al. | 435/188 |
| 4,043,872 | 8/1977 | Blakemore et al. | 435/7 |
| 4,043,989 | 8/1977 | Schneider et al. | 260/112 R |
| 4,045,420 | 8/1977 | Soffer et al. | 260/112 R |
| 4,046,636 | 9/1977 | Ullman et al. | 435/188 |
| 4,056,608 | 11/1977 | Ullman et al. | 424/12 |
| 4,058,511 | 11/1977 | Singh | 23/230 B |
| 4,064,151 | 12/1977 | Hedaya et al. | 260/448.2 |
| 4,065,354 | 12/1977 | Ullman et al. | 435/188 |
| 4,067,774 | 1/1978 | Rubenstein et al. | 435/188 |
| 4,069,105 | 1/1978 | Singh | 23/230 B |
| 4,121,975 | 10/1978 | Ullman et al. | 23/230 B |
| 4,123,431 | 10/1978 | Soffer et al. | 260/292 |
| 4,130,462 | 12/1978 | Rubenstein et al. | 435/7 |
| 4,134,792 | 1/1979 | Boguslaski et al. | 435/7 |
| 4,156,081 | 5/1979 | Singh et al. | 435/7 |
| 4,160,016 | 7/1979 | Ullman | 424/8 |
| 4,160,645 | 7/1979 | Ullman | 23/230 B |
| 4,161,515 | 7/1979 | Ullman | 424/12 |
| 4,171,244 | 10/1979 | Blakemore et al. | 435/188 |
| 4,174,384 | 11/1979 | Ullman et al. | 424/8 |
| 4,191,613 | 3/1980 | Ullman et al. | 435/188 |
| 4,193,983 | 3/1980 | Ullman et al. | 424/12 |
| 4,208,479 | 6/1980 | Zuk et al. | 435/7 |
| 4,213,893 | 7/1980 | Carrico et al. | 260/112.5 |
| 4,318,980 | 3/1982 | Boguslaski et al. | 435/188 |
| 4,318,983 | 3/1982 | Hornby et al. | 435/188 |

OTHER PUBLICATIONS

Gonnelli et al., "Interaction of S-Protein with S-Peptides-Tyroxine Conjucate", *Italian Journal of Biochemistry*, vol. 29 (1980), pp. 234–235.

J. F. Burd, R. C. Wong, J. E. Feeney, R. J. Carrico and R. C. Boguslaski, *Clin. Chem.*, 23, (1977), 1402.

F. Kohen, Z. Hollander and R. C. Boguslaski, *Jour. of Steroid Biochem.*, 11, (1979), 161.

F. Kohen, Z. Hollander, F. Yeager, R. J. Carrico and R. C. Boguslaski, *Enzyme-Labeled Immunoassay of Hormones and Drugs*, edit. by S. B. Pal, W. deGruiter, Berlin & NY, (1978), 67–79.

R. J. Carrico, J. E. Christner, R. C. Boguslaski and K. K. Young, *Anal. Biochem.*, 72, (1976), 271.

M. J. O'Sullivan, J. W. Bridges and V. Mark, *Annals of Clinical Biochemistry*, 19, (1977), 221.

Chemical Rubber Company *Enzyme Immunoassay*, edited by Edward T. Maggio, (1980), 105–134.

H. Rubsamen, R. Khandler and H. Witzel, Hoppe-Seyler's *Z. Physiol Chem.*, 355, (1974), 687.

F. M. Richards, *Proc. Nat'l. Acad. Sci. U.S.*, 44, (1958), 162.

F. M. Richards and P. J. Vithayahil, *J. Biol Chem.*, 234, (1959), 1459.

F. M. Richards and H. W. Wyckoff, *The Enzymes*, (P. D. Boyer, Ed.), Academic Press, 3d Ed., vol. 4, (1978), 647–806, London and New York.

G. W. Welling, J. A. Lenstra, J. J. Beintema, *FEBS Letters*, 63, (1979), 89.
M. C. Lin, *J. Biol. Chem.*, 245, (1970), 6726.
M. C. Lin, B. Gutte, S. Moore and R. B. Merrifield, *J. Biol. Chem.*, 245, (1970), 5169.
M. C. Lin, B. Guth, D. G. Caldi, S. Moore and R. B. Merrifield, *J. Biol. Chem.*, 247, (1972), 4768.
S. Lin, M. Villarego and I. Zabin, *Biochem. Biophys. Research Commun.*, 40, (1970), 249.
D. V. Marinkovic and J. N. Marinkovic, *Biochem, J.*, 155, (1976), 209.
S. L. Morrison and D. Zipser, *J. Mol. Biol.*, 50, (1970), 359.
J. V. Welply, W. Mandecki, A. V. Fowler and I. Zabin, *Biochem. Biophys. Res. Commun.*, 93, (1980), 223.
F. Celada and I. Zabin, *Biochem.*, 18, (1979), 404.
F. M. Finn and K. Hofmann, *Accounts of Chem. Research*, 6, (1973), 170.
A. Rochi, F. Marchiori, L. Maroder, A. Fontana and E. Scoffone, *Gazz. Chim. Ital.*, 96, (1966), 1537.
L. Maroder, A. Rochi, F. Marchiori, A. Fontana and E. Scoffone, *J. Amer. Chem. Soc.*, 91, (1961), 3921.
R. Rochi, L. Maroder, F. Marchiori, E. Ferrarese and E. Scoffone, *J. Amer. Chem. Soc.*, 90, (1968), 5885.
F. Marchiori, R. Rochi, L. Maroder and E. Scoffone, *Gazz. Chim. Ital.*, 96, (1966), 1549.
H. K. Kricheldorf, *Angew. Chem.*, 87, (1975), 517.
P. Cuatrecases, M. Wilchek and C. B. Anfinsen, "The Action of Staphyloccal Nuclease and Synthetic Substrates," *Synthetic Substrates of Staphyloccas Nuclease*, vol. 8, No. 6, Jun. 1969, pp. 2277–2283.
C. Cook, J. A. Kepler, H. Dix Christiansen, *Res. Comm. Chem. Path. Pharma.*, 5, (1973), 767.

*Primary Examiner*—Thomas G. Wiseman
*Attorney, Agent, or Firm*—George W. Rauchfuss, Jr.

[57] ABSTRACT

A highly sensitive, immunoassay method for determining the amount of an analyte in a sample containing a known analyte in an unknown concentration is provided. Sample; a polypeptide-labeled analog of the analyte, an antibody specific for said analyte, a polypeptide partner capable of non-covalently binding with the polypeptide-labeled analyte to form a complex having catalytic activity, and a substrate capable of being converted to a reporter molecule by the catalytic activity of said complex are brought together in a medium. The polypeptide-labeled analyte analog is capable of competitively binding to the antibody and the polypeptide partner, the antibody inhibiting the formation of a catalytically active complex in the absence of analyte, and the concentrations of the antibody, polypeptide partner and polypeptide-labeled analyte are such as to cause varying amounts of analyte to be directly related to the conversion of the substrate to the reporter molecule. Conversion of the substrate to the reporter molecule is then determined, and compared to conversions of substrate to reporter molecule obtained with known concentrations of the analyte.

34 Claims, 6 Drawing Figures

METHOD FOR CARRYING OUT NON-ISOTOPIC IMMUNOASSAYS, LABELED ANALYTES AND KITS FOR USE IN SUCH ASSAYS

RELATED APPLICATIONS

Gohlke, Hedaya, Kang and Mier, filed on Mar. 30, 1981 as Ser. No. 248,672, for Novel Chromogenic and/or Fluorogenic Substrates For Monitoring Catalytic or Enzymatic Activity.

Kang & Tolman, filed on Mar. 30, 1981 as Ser. No. 248,682, abandoned for A Method for Making Chromogenic and/or Fluorogenic Substrates for Use in Monitoring Catalytic or Enzymatic Activity.

Kang, filed on Mar. 30, 1981 as Ser. No. 248,688, for A Method for Making Chromogenic and/or Fluorogenic Substrates for Use in Monitoring Catalytic or Enzymatic Activity.

BACKGROUND OF THE INVENTION

1. Field of the Invention

This invention relates to the analysis of various compounds in biological fluids or the like and, more particularly, to certain novel labeled analytes and to methods of analysis using such labeled analytes.

2. Description of the Prior Art

For a variety of clinical purposes such as, for example, monitoring dosage schedules, monitoring hormone levels, checking for recent ingestion or following pharmacological dynamics of bioavailability, absorption, degradation or excretion, it is a great advantage to measure the concentration of various drugs or the like to the nanomolar or even picomolar level. As is known, radioimmunoassay can accomplish analyses of this type. To carry out an analysis, an acceptable kit or system must include an antiserum, a standard or known concentration of the compound (i.e.—analyte) to be measured, a radio-labeled derivative of the compound to be measured and a buffering agent or agents. The antiserum is produced by bleeding animals which have been immunized by innoculation, for example, with the hapten—protein conjugate (immunogen) corresponding to the compound to be measured.

As is well known, the technique of radioimmunoassay, in general, measures the competition between radioactively labeled analyte and unlabeled analyte for binding sites on the antibody in the antiserum. By adding to the antiserum known amounts of the analytes to be assayed and a radiolabeled analog, a dose—response curve for bound or free analyte vs. concentration of analyte is constructed. After this immuno-calibration has been carried out, unknown concentrations can then be compared to the standard dose-response curve for assay. Crucial to this type of assay is the existence of radioactive analytes which compete effectively with non-radioactive analytes. Accordingly, in order to obtain the maximum precision, accuracy, sensitivity, specificity and reproducibility of the assay, purified, well-characterized synthetic radioactive analytes are required.

Several deficiencies in radioimmunoassay methodology have been identified. First of all, it is necessary to make a physical separation of the antibody-bound, radiolabeled analyte from the free radiolabeled analyte. Further, the methodology is considered rather labor intensive; and the equipment required is likewise relatively expensive, is not uniformly available and further requires the use of highly trained and skilled technicians to accurately carry out such assays. Likewise, the radioisotopically-labeled analytes are relatively unstable and expensive and pose an increasingly severe waste disposal problem owing to radiation exposure hazards associated with the commonly used radioisotopic labels. Despite these shortcomings, the use of radioimmunoassay has grown considerably.

The substantial recent growth in the use of radioimmunoassay in clinical laboratories has, however, spurred the development of variants which overcome the deficiencies of the radioimmunoassay methodology as described herein. The approaches which have been developed to overcome these deficiencies primarily involve the use of enzyme or fluorescent labels instead of radioisotopic labels, preferably coupled with conditions allowing for measuring a chemical distinction between bound and free fractions of labeled analyte which leads to the elimination of the requirement for physical separation. Immunoassays having the latter simplifying and advantageous feature are referred to as homogeneous immunoassays as opposed to heterogeneous immunoassays where physical separation is required.

Thus, homogeneous immunoassay systems have been developed which are based on the use of an enzyme-labeled analyte where the enzymatic activity of the label is decreased when complexation with the antibody occurs. Unlabeled analyte whose concentration is to be determined displaces the enzyme-labeled analyte bound to the antibody, thus causing an increase in enzymatic activity. Standard displacement or dose-response curves are constructed where increased enzymatic activity (monitored spectrophotometrically using what has been termed a "substrate" which ultimately produces a unique chromophore as a consequence of enzyme action) is plotted against increased analyte concentration. These are then used for determining unknown analyte concentrations. The following U.S. patents have been issued in the field of homogeneous enzyme immunoassay: Nos. 3,817,837; 3,852,157; 3,875,011; 3,966,556; 3,905,871; 4,065,354; 4,043,872; 4,040,907; 4,039,385; 4,046,636; 4,067,774; 4,191,613; and 4,171,244. In these patents, the label for the analyte is described as an enzyme having a molecular weight substantially greater than 5,000. Commercialization of this technology has been so far limited to applications where the analytes are relatively small in molecular size at fluid concentrations of the analyte greater than $10^{-10}$M. These limitations result from the fact that the commonly used enzyme labels derived from large polypeptide analytes are not inhibited by binding to the anti-analyte antibody. Also, sensitivity limitations result from the lack of a fluorometric reporter molecule resulting from enzyme action and from the presence of serum interference at low concentrations, such as, for example, endogenous enzyme. Furthermore, the enzyme labels can be difficult to prepare reproducibly and to satisfactorily purify.

As a consequence of the limitations of the homogeneous enzyme immunoassay techniques described above, considerable effort has been devoted towards developing more sensitive homogeneous immunoassays using fluorescence. These have been primarily directed at assays for the larger sized molecules such as immunoglobulins or polypeptide hormones such as insulin. The following U.S. patents have been issued for this type of assay: Nos. 3,998,943; 3,996,345; 4,174,384; 4,161,515;

4,208,479 and 4,160,016. The label in most of these patents involves an aromatic fluorescent molecule bound either to the analyte or to the antibody. All likewise involve various methods of quenching fluorescence through antibodies or other fluorescent quenchers so that the extent of quenching is related to the amount of analyte present in the sample. Assays based on these approaches have not been commercialized probably owing to the difficulty in preparing satisfactorily plurified fluorescent labeled-antibodies or analytes or related quencher-labeled species. Also, background fluorescence in serum may occur as well as serum-induced quenching. Still further, since such methods are not enzyme amplified, satisfactory sensitivity may be a problem.

Still other U.S. patents in this field which cannot be readily categorized in terms of the type of the immunoassay include: Nos. 3,935,074; 4,130,462; 4,160,645 and 4,193,983. The approach set forth in U.S. Pat. No. 4,160,645 includes the use of an electron transfer catalyst as a label. The catalyst (label) is deactivated by bonding to antibody.

Additional U.S. patents directed to the preparation of hapten conjugates to be used for the preparation of antibodies include: Nos. 3,884,898; 3,843,696; 4,045,420; 3,888,866; 3,917,582; 4,025,501; 4,043,989; 4,058,511; 4,069,105; 4,123,431; and 4,186,081. All of these patents relate to analyte derivatives and corresponding polypeptide conjugates wherein the polypeptide is antigenic and has a molecular weight in the range of 5,000 to $10^6$. Proteins such as albumin and globulin are specifically set forth.

Also, pretreatment methodologies for homogeneous enzyme immunoassays have been provided. U.S. patents in this area include: Nos. 3,856,469; 4,056,608 and 4,121,975.

A further type of methodology which may be described as a reactant-labeled fluorescent immunoassay involves the use of a fluorescent labeled analyte designed so that a fluorescent product is released when it is enzymatically hydrolzyed. Antibody to the analyte portion of the molecule, however, inhibits enzymatic hydrolysis. Consequently, by the law of mass action, fluorescence is enhanced in the presence of increased analyte due to enzymatic hydrolysis of the displaced, fluorescent labeled analyte. As an example, a labeled analyte is β-galactosyl-umbelliferone-sisomicin. The enzyme β-galactosidase cleaves the sugar from the umbelliferone moiety which can then fluoresce. Publications which describe this methodology include: J. F. Burd, R. D. Wong, J. E. Feeney, R. J. Carrico and R. C. Boguolaski, *Clin. Chem.*, 23, 1402(1977); Burd, Carrico, M. C. Fetter, et al., *Anal. Biochem.*, 77, 56 (1977) and F. Kohen, Z. Hollander and Boguolaski, *Jour. of Steroid Biochem.*, 11, 161 (1979).

Yet another type of homogeneous non-isotopic immunoassay is disclosed in U.S. Pat. No. 4,213,893, utilizing cofactor-labeled analytes. This involves labeling an analyte by linking it to a derivative of NAD (i.e. - nicotinamide-6(2-aminoethylamino)-purine dinucleotide). The labeled cofactor retains its reactivity with dehyrogenases (e.g.—alcohol dehydrogenase, malate dehydrogenase, viz. —ADH, MDH) in cycling reactions for estriol as the analyte. Ultimately, the NADPH which is formed in these reactions is monitored fluorometrically and is a measure of the cycling rate. The NADPH is reduced in the presence of estriol antibody owing to complexation of the labeled cofactor. Thus, the cycling rate is directly related to the amount of estriol and was found to increase linearly with increasing amounts of estriol. This is described in a 1978 publication by F. Kohen, Z. Hollander, F. Yeager, R. J. Carrico, and R. C. Boguolaski, pp. 67–79, "Enzyme-labeled Immunoassay of Hormones and Drugs", edited by S. B. Pal, Walter de Gruiter, Berlin and New York. A similar system has been described for biotin and 2,4-dinitrofluorobenzen analytes using lactic dehydrogenase and diaphorase as cycling enzymes (R. J. Carrico, J. E. Christner, R. C. Boguolaski and K. K. Young, *Anal. Biochem.*, 72, 271 (1976)). It has been pointed out that the methodology may be subject to interference by endogenous co-factors and degrading enzymes common to bodily fluids (M. J. O'Sullivan, J. W. Bridges and V. Mark, *Annals of Clinical Biochemistry*, 19, 221 (1977)).

Yet another type of immunoassay technique utilizes an enzyme modulator as a label, viz.—an enzyme inhibitor or an allosteric effector. A number of enzyme modulators are listed along with their respective enzymes in U.S. Pat. No. 4,134,792. When a specific antibody binds to an enzyme modulator-labeled analyte, the enzyme modulator can no longer inhibit or otherwise affect the activity of an enzyme in the incubating mixture. Thus, displacement of the enzyme modulator-labeled analyte by free analyte restores inhibition or the allosteric effect of the enzyme modulator.

In a recent work entitled "Enzyme Immunoassay", published by Chemical Rubber Company, 1980, edited by Edward T. Maggio, the chapter entitled "Principles of Homogeneous Enzyme-Immunoassay", pages 105–134, makes reference to the use of ribonuclease A as an enzyme label for human immunoglobulin G. Although details are not presented, the authors conclude that ribonuclease A has potential for use as a label in protein homogeneous enzyme-immunoassays. However, the authors also note that, unfortunately, the ubiquitous nature of ribonuclease A represents a serious potential for interference from endogenous enzyme in serum assays, and limits the practical utility of the procedure.

Further, considerable investigation of the structure and properties of ribonucleases has been carried out. For example, many organic compounds have been utilized heretofore for monitoring the catalytic activity of ribonuclease. Such organic compounds, or substrates, as they are commonly referred to, include ribonucleic acid itself, cyclic phosphate diesters, and monoribonucleotide compounds which exhibit the same or similar structural constraints as those expressed by the natural substrate.

Still other compounds have been utilized for kinetically monitoring ribonuclease activities. Such compounds include 3'-uridylic acid phosphodiesters of 1-naphthol, 5-hydroxynaphthol, and 1-4 methoxyphenol, H. Rubsamen, R. Khandler, and H. Witzel (Hoppe-Seyler's *Z. Physiol. Chem.*, 355, 687 (1974)). However, the hydrolysis product is monitored directly in the ultraviolet region, which is not sufficiently sensitive for analyses in the nanomolar or picomolar range and where interferences derived from clinical samples may occur. Further these substrates are difficult to prepare and require numerous steps, including lengthy chromatographic procedures.

Also, the cleavage of ribonucleases to polypeptide fragments has been investigated. For example, the action of subtilisin, a bacterial protease, on bovine pancreatic ribonuclease (ribonuclease A) is known. It has thus been found that a short 20 residue polypeptide and a long 104 residue polypeptide resulted as a consequence of the cleavage at the 20th peptide bond (counting from the amino terminus) of the ribonuclease A. The former is called the S-peptide while the latter is referred to as the S-protein (F. M. Richards, *Proc. Nat'l. Acad. Sci. U.S.*, 44 162 (1958); F. M. Richard and P. J. Vithayahil, *J. Biol. Chem.*, 234, 1459(1959)). It is likewise known that the two polypeptides readily combine to form a non-covalent complex ($K=10^{-8}M$) which retained the same catalytic activity of the original enzyme, ribonuclease A, towards a variety of substrates such as RNA or cytidine 2′, 3′-phosphate diester. However, insofar as is known, this knowledge has not heretofore been utilized in developing immunoassay techniques.

Thus, despite the considerable recent activity in the field of homogeneous immunoassay, there remains the need for further development which can overcome various shortcomings of the presently used techniques. This is perhaps evident from the comparatively restricted commercial usage of non-isotopic immunoassay techniques despite the apparent broad potential. Thus, despite their well-recognized deficiencies, radioimmunoassay techniques continue to be widely used simply because satisfactory alternative techniques are not commercially available.

It is accordingly an object of the present invention to provide a homogeneous immunoassay technique which is broadly applicable to a wide range of analytes. A related and more specific object provides a homogeneous immunoassay technique which is thus not restricted to use with relatively small molecular weight analyte molecules.

A further object lies in the provision of a homogeneous immunoassay method which does not require the use of relatively high molecular weight labels. A related object is to provide labeled analytes which can be easily prepared, are readily purified and are relatively stable.

Another object of the present invention provides a homogeneous immunoassay method which is capable of operating in either a spectrophotometric or a fluorometric detection mode, using a substrate common to either mode, if desired.

A still further object of this invention is to provide a homogeneous immunoassay method which is capable of achieving superior sensitivity. A related and more specific object involves an essay with a fluorometric detection mode which is amplified by catalytic turnover of the substrate.

A still further object lies in the provision of a homogeneous immunoassay method which can be readily adapted for use in commercially available automatic analyzers, such as, for example, what are commonly termed "centrifugal fast analyzers".

Another object of the present invention is to provide a homogeneous immunoassay technique which is readily adaptable to automatic data reduction. A related and more specific object provides such an immunoassay technique wherein a dose-response curve satisfactory for automatic data reduction can be achieved.

A further object of this invention provides a homogeneous immunoassay technique wherein the methodology is sufficiently flexible to minimize problems such as, for example, potential interferences and the like.

Other objects and advantages of the present invention will become apparent from the following detailed description and from the drawings, in which.

Figure 1:
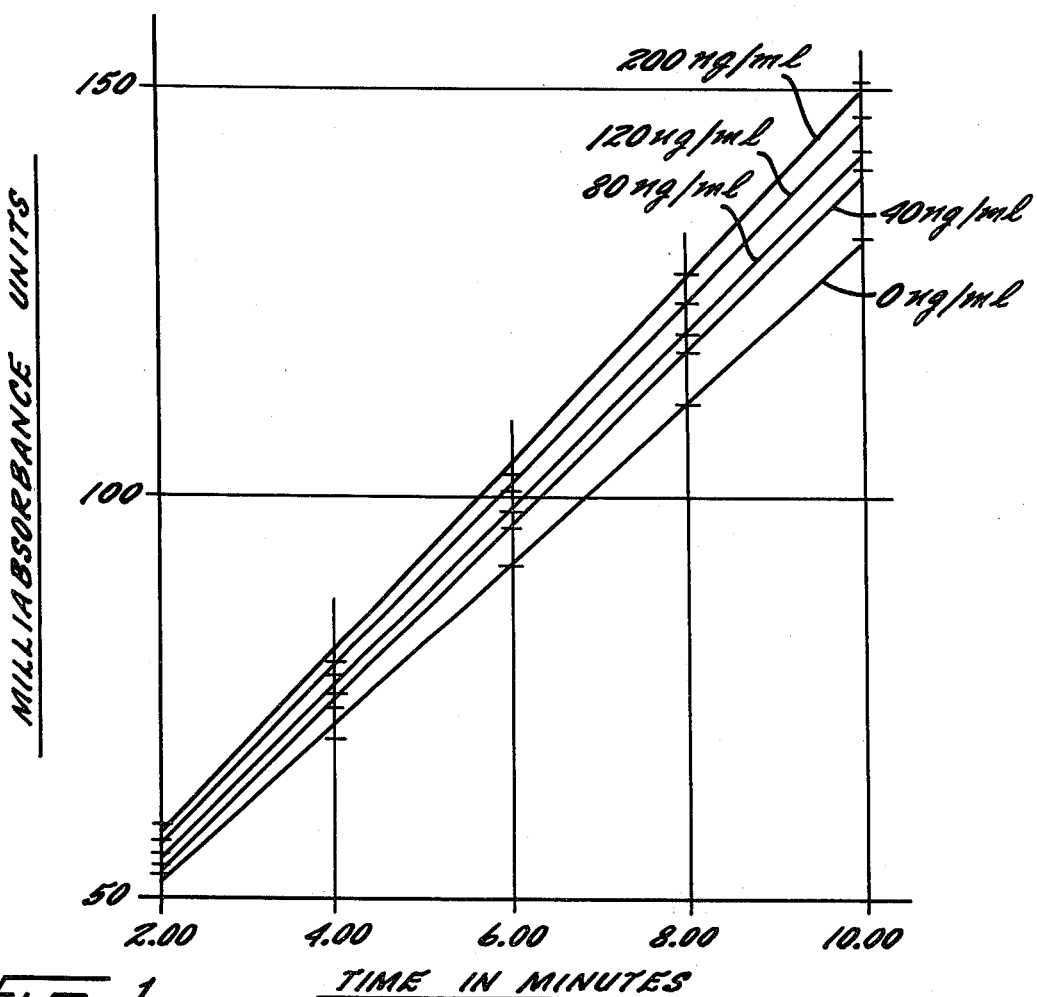
FIG. 1 is a graph of absorbance versus time for various concentrations of the analyte thyroxine and which illustrate both the linearity of rate measurements as well as the increase in rate (slope) with increasing thyroxine concentration.

While the invention is susceptible to various modifications and alternative forms, there will herein be described in detail the preferred embodiments. It is to be understood, however, that it is not intended to limit the invention to the specific forms disclosed. On the contrary, it is intended to cover all modifications and alternative forms falling within the spirit and scope of the invention as expressed in the appended claims. For example, while the labeled analytes of the present invention will be principally described in conjunction with a homogeneous immunoassay technique, it should be appreciated that the present invention is equally applicable to use in a heterogeneous immunoassay where antibody-bound and free fractions of the polypeptide labeled analyte are separated prior to spectrophotometric or fluorometric measurement.

SUMMARY OF THE INVENTION

In general, the present invention is predicated on the discovery that a highly sensitive, immunoassay method can be provided by utilizing a polypeptide pair, one member serving as a label for the analyte and the other being present in the mixture. The labeled analyte which results, when combined with its polypeptide partner, forms a complex which possesses catalytic activity towards particular chromogenic or fluorogenic substrates. Furthermore, and importantly, the catalytic activity of such labeled analytes is severely inhibited in the presence of antibody to the analyte. This inhibition is lifted when increasing concentrations of the analyte are added to the mixture. Accordingly, a displacement curve can be constructed which relates the catalytic activity, or a function of the catalytic activity, to the analyte concentration; and this reference or standard curve then allows the determination of unknown analyte concentrations.

The ability to provide a satisfactorily sensitive immunoassay method depends both upon selection of an appropriate polypeptide pair as well as certain parameters including the equilibrium constants for the reaction of the analyte with the antibody and the reaction of the labeled analyte with its polypeptide partner as well as the relative concentrations of the antibody, the labeled analyte and the polypeptide partner, as will be discussed herein.

DETAILED DESCRIPTION

Assay Protocol

A wide variety of protocols can be used in conjunction with the present invention. In general, the homogeneous immunoassay method of the present invention comprises (a) bringing together in a medium, (1) a sample containing an analyte, (2) a polypeptide labeled analyte, (3) an antibody specific for the analyte, (4) a polypeptide partner capable of non-covalently binding with the polypeptide of the labeled analyte to form a complex having catalytic activity and (5) a substrate capable of being converted to a reporter molecule by the catalytic activity of the complex, (b) determining the rate or extent of conversion of the substrate to the reporter molecule and (c) comparing the rate or extent of conversion to those obtained in mediums having known amounts of analyte. The order of addition of the materials may be varied as desired; and, in some instances, it may be desirable to provide incubating steps.

The assay may be advantageously carried out by utilizing any of a wide variety of commercially available apparatus. For example, to carry out analyses using spectrophotometric techniques, it has thus been found suitable to use the CentrifiChem ® 400 and 500 fast analyzers manufactured by Union Carbide Corporation, the assignee of the present invention. This type of analyzer is, in general, described in Norman G. Anderson, "Analytical Techniques for Cell Fractions XII. A Multiple-Cuvet Rotor for a New Microanalytical System", *Analytical Biochemistry*, 28, pp. 545-562 (1969). Suitable fluorometric apparatus is likewise commercially available.

Use of the exemplary fast analyzers involves, in one protocol, pipetting a sample containing analyte whose concentration is to be determined, antibody, and polypeptide labeled analyte into the sample well of the transfer disc of the analyzer, pipetting polypeptide partner and substrate into the reagent well of the transfer disc, incubating, if necessary, the mixture in the sample well and spinning the transfer disc while analyzing the recovery of catalytic activity of the labeled analyte complex by monitoring the rate of conversion of substrate to the reporter molecule by suitable means, such as, for example, spectrophotometric techniques.

It should be noted that the order of addition of reagents, is not normally critical. Thus, the addition order in connection with the protocol for centrifugal fast analyzers may be altered, if desired. For example, the addition of partner polypeptide and labeled analyte may be interconverted; and this would correspond to a delayed addition of labeled analyte which could enhance assay sensitivity. This allows for increased pipetting efficiency since mixed solutions rather than single reagent components may be pipetted. In this instance, three pipetting operations are involved: (1) analyte sample, (2) antibody and polypeptide partner and (3) labeled analyte and substrate. Accordingly, with the commercial fast analyzers previously described, sufficient automatic pipetters are available to allow carrying out the three operations described in one cycle.

The time of any incubation step, if used, will vary depending, primarily, on the nature of the analyte. Incubation establishes an equilibrium or kinetic distribution of antibody-bound and free labeled analyte which is related to the concentration of analyte. Small analytes, such as drugs or drug metabolites generally require short incubation periods, whereas relatively large molecular weight analytes, such as, for example, polypeptide hormones, may require substantially longer incubation periods, owing to diffusion-controlled rate of complexation with antibody. Thus, the incubation period can be varied from about one minute to as long as about 24 hours. Furthermore, it is not necessary for the incubating mixture of analyte, labeled analyte and antibody to reach equilibrium. A kinetic immunoassay is possible where the incubation times for all incubating mixtures and the corresponding measurement of the rate of reporter molecule product formation are kept constant and identical. A kinetic assay reduces the overall time required for analysis and allows for the above-mentioned interconversion of labeled analyte and partner polypeptide.

The rate of product appearance, that is, reporter molecule formation, may be monitored by either spectrophotometric or fluorometric photometers, depending upon the nature of the analyte. For analytes which are present in concentrations greater than about $10^{-9}$ M, spectrophotometric detection is preferred, whereas fluorometric detection is preferred for analytes present at lower concentration levels, because of the inherent greater sensitivity of the fluorometric method. In the alternative, by monitoring rates for longer periods of time, for example, 35 minutes or greater, if such longer periods are acceptable, spectrophotometric detection may be utilized for analytes and concentrations less than $10^{-9}$ M.

By following the typical assay protocols of the present invention, and by utilizing increasing known analyte concentrations, it is possible to construct a standard or reference curve of catalytic activity (e.g., rate of formation of reporter molecule) or alternatively, a function of catalytic activity versus analyte concentration. The standard or reference curve may then be utilized to determine an unknown analyte concentration after measuring the rate of formation of reporter molecule at the same conditions used to construct the standard curve.

When the labeled analyte, partner polypeptide, and antibody are present together in the sample, the polypeptide labeled analyte is capable of binding, in a competitive fashion, either to the antibody or to the polypeptide partner. Catalytic activity is provided when the polypeptide labeled analyte binds to its polypeptide partner, but catalytic activity is inhibited (i.e., not expressed or provided) when the polypeptide labeled analyte binds to the antibody. Due to the equilibrating reactions of the system, and by the law of mass action, analyte displaces polypeptide labeled analyte bound to the antibody; and, as a result, there is available in the sample unbound labeled analyte which is capable of binding with its polypeptide partner. Thus, in the absence of analyte, reduced catalytic activity is expressed. However, where analyte is present in the sample, increased catalytic activity occurs which can be monitored. Since catalytic activity will be diminished or inhibited when the labeled analyte is bound to the antibody, but will be recovered in the presence of analyte, the catalytic activity of the solution will be directly related to the concentration of analyte present in the sample.

The methodology of the present invention involves a consideration of, basically, six equations. Fundamental to the methodology, as is the case with any immunoassay technique, is that the rates of reaction (or equilibration) of antibody to the labeled and unlabeled analyte be generally the same. These two reactions are set forth below:

$$A + Ab \rightleftharpoons A.Ab \quad (1)$$

$$A\text{-}PP_1 + Ab \rightleftharpoons A\text{-}PP_1.Ab \quad (2)$$

wherein A is the analyte, Ab is the antibody or receptor protein specific for the analyte, A.Ab is the complex formed by the reaction of the analyte and antibody, A-$PP_1$ is the analyte or analyte analog labeled with one of the polypeptide partners and A-$PP_1$.Ab is the complex formed by the reaction of the labeled analyte and antibody. Obviously, if the rates of reactions (1) and (2) are not generally the same, competitive binding will not result.

As noted herein, the presence of analyte in a sample displaces polypeptide labeled analyte bound to the antibody so the unbound labeled analyte can then bind with its polypeptide partner. The latter reaction is depicted below:

$$A\text{-}PP_1 + PP_2 \rightleftharpoons A\text{-}PP_1.PP_2 \quad (3)$$

wherein A-$PP_1$ is the labeled analyte as previously described, $PP_2$ is the polypeptide partner and A-$PP_1$.$PP_2$ is the non-covalent catalytic complex. The non-covalent catalytic complex serves to catalyze the conversion of a substrate to a reporter molecule as is depicted below:

$$S \xrightarrow{A-PP_1.PP_2} P \quad (4)$$

wherein S is the substrate and P is the reporter molecule catalytically derived from S.

Conceptually, the other two reactions which must be considered are:

$$A\text{-}PP_1.Ab + PP_2 \rightleftharpoons A\text{-}PP_1.Ab.PP_2 \quad (5)$$

$$S \xrightarrow{A-PP_1.Ab.PP_2} P \quad (6)$$

wherein A-$PP_1$.Ab is the bound labeled analyte, $PP_2$ is the polypeptide partner, A-$PP_1$.Ab.$PP_2$ is the theoretical ternary complex formed by the reaction of the labeled analyte, antibody and the polypeptide partner, S is the substrate and P is the reporter molecule. To provide satisfactory sensitivity, either the formation of the ternary complex in reaction (5) must be minimal or the ternary complex should not catalytically convert, to any significant extent, the substrate to the product in accordance with reaction (6). Stated another way, if whatever amount of ternary complex is formed in reaction (5) results in significant amounts of the reporter molecule, P, being formed via reaction (6), the amount of P being formed in reaction (4) will not be suitably related to varying amounts of the analyte present.

In considering the effects of these six reactions, the concentrations of the antibody, the polypeptide partner and the labeled analyte should be selected in a particular assay so that varying amounts of analyte will be reflected in the conversion of the substrate to the reporter molecule. The equilibrium constants for reactions (1) through (3) must also be taken into account.

As a guide for designing a particular assay, the relationships desired may be illustrated by the following inequalities, derived from a mathematical analysis of the scheme incorporating certain simplifying assumptions:

$$K_3[Ab]/K_1 \geqq [PP_2] \geqq [A\text{-}PP_1] + K_3$$

wherein $K_1$ and $K_3$ are the equilibrium constants for reactions (1) and (3), [Ab] is the concentration of antibody, [$PP_2$] is the concentration of the polypeptide partner and [A-$PP_1$] is the concentration of the labeled analyte. This mathematical analysis assumes that $K_1$ and $K_2$ (the equilibrium constant for reaction (2)) are identical and that reactions (5) and (6) do not proceed at all.

With respect to the expression $K_3[Ab]/K_1$, an overall value of much less than a factor of 1 less than [$PP_2$] will provide only a minimal response in relation to varying amounts of the analyte concentration because the result would be that little bonding to antibody would occur. Stated another way, the catalytic species formed in reaction (3) would form independently of the analyte concentration so that it would be difficult, as best, to distinguish between varying amounts of analyte present regardless of the analyte concentration. This follows since the product of reaction (2) would be formed in only minimal amounts. On the other hand, if either the concentration of antibody is too high or the equilibrium constants are such that the overall values of the expression is in excess of 1,000 times greater than [$PP_2$], then the catalytically active species in reaction (3) would not be formed in amounts satisfactory to respond to varying analyte concentrations. It will be accordingly generally desirable to design the assay with the expression $K_3[Ab]/K_1$ being about 2 to 100 times greater than [$PP_2$], preferably about 5 to 25.

Further, there will be little sensitivity when the concentration of $PP_2$ is too high in relation to the expression $K_3[Ab]/K_1$ because the reaction of the labeled analyte with its polypeptide partner, viz. - reaction (3), would be pushed to too great an extent compared to its reaction with antibody, viz. - reaction (2). The result would again be that varying amounts of analyte concentration could not be satisfactorily distinguished. If the concentration of the polypeptide partner is too low in relation to the expression $K_3[Ab]/K_1$, the reverse situation occurs. There will be an inadequate amount of the product in reaction (3), regardless of the analyte concentration. It is thus generally desirable to maintain the concentration of the polypeptide partner in the range of about a factor of 2 to 100 times less than the value of the expression $K_3[Ab]/K_1$, preferably about a factor of 5 to 25 times less.

Similarly, with regard to the concentration of labeled analyte and $K_3$, the concentration of the labeled analyte should be within a factor of about 10 to 100 of that of the analyte concentration expected.

The design of an assay in accordance with the present invention is, in general, similar to what is involved in the design of a typical immunoassay. As an example of designing an assay pursuant to this invention, the preliminary starting point involves securing: (1) a suitable antisera or antibody for the analyte involved, (2) the labeled analyte A-$PP_1$ and (3) the polypeptide partner $PP_2$.

The concentration of A-$PP_1$ is first fixed at generally the same as that of the anticipated analyte concentration. Next, the concentration of $PP_2$ is set at a value equal to or slightly greater than $K_3$. This will be, in most cases, about $10^{-8}$ M for the polypeptide pair consisting of the labeled S-peptide and S-protein. An amount of substrate S should be selected which will be high enough to provide, where a spectrophotometric mode is used for detection, a linear rate of at least about 10 milliabsorbance units per minute.

A conventional titration curve for the antibody is then developed measuring the precent of inhibition vs. antibody dilution using the appropriate labeled analyte and $PP_2$ concentrations as determined above. Typically, a concentration of antibody is selected which provides about a 50 percent inhibition ($\pm$ 20 or 30 percent) although an inhibition as low as 10 percent or so may be useful.

Standard concentrations of the analyte that mimic the expected concentration range for the analyte are prepared and then used with the parameters previously fixed to provide a reference displacement curve. This curve should then be examined to determine whether appropriate sensitivity is provided over the expected concentration range.

If greater sensitivity at the higher portion of the concentration range is desired, this can generally be provided by increasing the antibody concentration. Whatever increase is selected should be determined with the qualitative inequalities previously described as a guide.

When higher sensitivities at the lower portion of the range are desired, decreasing the antibody concentration should be helpful. Additionally, and again using the qualitative inequalities as a guide, it may be useful to decrease the concentration of $PP_2$ and the labeled analyte.

Further fine tuning may be achieved, if desired, by modifying the equilibrium constants $K_1$, $K_2$ and $K_3$ so as to increase or decrease the binding of the antibody to the analyte (and labeled analyte) and/or the non-covalent binding of the labeled analyte to its polypeptide partner. The further parameters introduced by this invention, i.e. - the concentration of $PP_2$ and the reaction of A-$PP_1$ and $PP_2$, provide additional means over and above most, if perhaps not all, prior immunoassay technology for fine tuning which contributes to the versatility characteristics of the present invention.

Suitable attention to the parameters discussed herein thus allows one to insure that the particular assay will have the desired sensitivity to varying amounts of analyte concentration.

Analytes

Theimmunoassay method of the present invention may be utilized in determining the quantitative presence of a wide variety of analytes. Analytes potentially suitable for determination by the method of this invention include, in general, complex organic molecules which are present in, or extractable into, an aqueous medium at a concentration level to at least about $10^{-12}$ M. The concentration limit results from the present practical detection limit of a fluorescent reporter molecule and the avidity or binding constant of the anti-analyte antibody.

Indeed, the present invention may be used for any analyte for which any prior immunoassay may be utilized. Moreover, conceptually, the present invention may be employed for determining the concentration of any analyte for which a specific receptor or binding protein is available. Obtaining such receptor or binding proteins becomes very difficult with extremely low molecular weight analytes, e.g. - less than about 100 or so. On the other hand, with relatively large molecular weight analytes, e.g. - about $10^6$ or so, care should be exercised in labeling the analyte in accordance with this invention to insure that satisfactory inhibition of catalytic activity is provided.

Analytes with which the method of the present invention may be utilized, and for which specific receptor or binding proteins are available, thus include, for example, drug and drug metabolites, opiates, narcotics, steroids, vitamins, hormones including polypeptide hormones, tumor associated antigens, immunoglobins, enzymes, industrial pollutants, pesticides and their metabolites, food additives, herbicides and their metabolites, flavoring agents, and food poisons. More particularly, the immunoassay method of the present invention may be used to assay the full range of the following analytes, in their respective concentrations: dilantin, cannabinoids, gentamicin, tobramycin, methotrexate, digitoxin, thyroxine, testosterone, cortisol and immunoglobins in a concentration range (in human serum) of from about $10^{-6}$ M to about $10^{-8}$ M; triiodothyronine, digoxin, folic acid, angiotensin II, progesterone, and prostaglandin F2, in the concentration range (in human serum) of from about $10^{-8}$ M to about $10^{-9}$ M; estradiol, vitamin $B_{12}$, and growth hormone in the concentration range (in human serum) of from about $10^{-9}$ M to about $10^{-10}$ M; insulin, parathyroid hormone, thyroid stimulating hormone, calcitonin, gastrin, luteinizing hormone, follicle stimulating hormone, glucagon, human chorionic gonadotropin, and aldosterone in the concentration range (in human serum) of from about $10^{-10}$ M to about $10^{-11}$ M; and carcinoembryonic antigen, in the concentration range (in human serum) of from about $10^{-11}$ M to about $10^{-12}$ M.

At present, most of the analytes set forth herein are currently determined by clinical radioimmunoassay using heterogeneous protocols. The immunoassay methodology of this invention potentially can assay the full range of analytes set forth herein without requiring the use of expensive, hazardous and unstable radionuclide labels. Use of complex gamma or scintillation counters is likewise avoided.

Polypeptide Partners

Suitable polypeptide pairs must meet the following functional characteristics: (1) at least one member must be capable of covalently bonding to an analyte or analyte analog to form a polypeptide labeled analyte, (2) the labeled analyte must compete with analyte for antibody, (3) the labeled analyte, upon combination with the polypeptide partner, provides catalytic activity sufficient to convert a substrate to a reporter molecule in adequately detectable amounts, and (4) for homogeneous immunoassay, the recovery of catalytic activity associated with the combination of the labeled analyte with its polypeptide partner is inhibited by complexation of the labeled analyte with antibody.

Conceptually, the combination phenomenon described above in requirement (3) is associated with the multiple intrachain interactions within enzymatic proteins which leads to stable, three dimensional structures and the formation of specific active sites. Such multiple intrachain interactions, which are largely non-covalent in nature, are, preferably, of sufficient integrated bonding strength so as to allow for reconstituted of the active sites even in the absence of a covalent bond along the backbone peptide chain.

Suitable polypeptide pairs, in accordance with one aspect of this invention, may be provided by cleaving various enzymes to provide two fragments. For example, the products formed by the enzymatic cleavage of staphylococcal nuclease and the enzymatic cleavage of pancreatic ribonucleases of the cow, rat, dromedary, and kangaroo, with various enzymes, such as, for example, subtilisin, pepsin and carboxypeptidase, provide suitable polypeptide pairs.

Alternately, one partner of a suitable polypeptide pair may be obtained genetically from a mutant bacterial strain as in the case of the M15 protein from the Z-deletion mutant strain from *Escherichia coli*. This protein recovers β-galactosidase activity in the presence of a small thermal or cyanogen bromide generated fragment of β-galactosidase (designated CB2). The phenomenon is referred to as complementation in vitro.

The polypeptide pair derived from the subtilisin-induced cleavage of ribonuclease A (of the cow) consists of the S-peptide or 20 amino acid fragment, and the much more complex S-protein which consists of 104 amino acid residues. These fragments result from the cleavage of ribonuclease A at the twentieth peptide bond, counting from the amino terminus of the ribonuclease A. The S-peptide has the following structure (F. M. Richards and H. M. Wyckoff in the Enzymes (Boyer, P. D. ed. 3rd ed., Vol. 4, pp. 647–806, Academic Press, London and NYC):

| H | Lys | Glu | Thr | Ala | Ala | Ala | Lys | Phe | Glu | Arg | Gln | His | Met | Asp | Ser |
|---|-----|-----|-----|-----|-----|-----|-----|-----|-----|-----|-----|-----|-----|-----|-----|
|   | 1   | 2   | 3   | 4   | 5   | 6   | 7   | 8   | 9   | 10  | 11  | 12  | 13  | 14  | 15  |
|   | Ser | Thr | Ser | Ala | Ala | OH  |     |     |     |     |     |     |     |     |     |
|   | 16  | 17  | 18  | 19  | 20  |     |     |     |     |     |     |     |     |     |     |

S-Peptide 1-20

The S-protein, as is likewise known, has the following structure:

S-Protein (21-124)

In the descriptions of the S-Peptide and S-Protein set forth herein, the conventional abbreviations have been employed.

Cross-species hybrids, e.g. - where $PP_1$ is derived from an enzyme from a dissimilar animal species than that for $PP_2$, are also suitable. For example, the S-Peptide derived from the dromedary, kangaroo and rat, also have been found to have catalytic activity in the presence of S-protein, specifically bovine S-protein or dromedary S-protein. (J. A. Lenstra, J. J. Beintema, FEBS Letters, 63 89 1976; G. W. Welling, G. Groen, D. Gakel, W. Gaastra, and J. J. Beintema, FEBS Letters, 40 134 1974). The polyamino acids of these species are set out below:

| | | | | Dromedary S-peptide: | | | | | | | | | | |
|---|---|---|---|---|---|---|---|---|---|---|---|---|---|---|
| H | Ser | Glu | Thr | Ala | Ala | Gln | Lys | Phe | Gln | Arg | Gln | His | Met | Asp | Ser |
|   | 1   | 2   | 3   | 4   | 5   | 6   | 7   | 8   | 9   | 10  | 11  | 12  | 13  | 14  | 15  |
|   | Tyr | Ser | Ser | Ser | OH  |     |     |     |     |     |     |     |     |     |     |
|   | 16  | 17  | 18  | 19  |     |     |     |     |     |     |     |     |     |     |     |
| | | | | Kangaroo S-peptide: | | | | | | | | | | |
| H | Glu | Thr | Pro | Ala | Glu | Lys | Phe | Gln | Arg | Gln | His | Met | Asp | Thr | Gln |
|   | 2   | 3   | 4   | 5   | 6   | 7   | 8   | 9   | 10  | 11  | 12  | 13  | 14  | 15  | 16  |
| H | Thr | Ser | Thr | Ala | Ser | OH  |     |     |     |     |     |     |     |     |     |
|   | 17  | 18  | 19  | 20  | 21  |     |     |     |     |     |     |     |     |     |     |
| | | | | Rat - 13 residues: | | | | | | | | | | |
| H | Glu | Ser | Ser | Ala | Asp | Lys | Phe | Lys | Arg | Gln | His | Met | Asp | OH  |     |
|   | 2   | 3   | 4   | 5   | 6   | 7   | 8   | 9   | 10  | 11  | 12  | 13  | 14  |     |     |
| | | | | Rat - 17 residues: | | | | | | | | | | |
| H | Gly | Gln | Ser | Arg | Gln | Ser | Ser | Ala | Asp | Lys | Phe | Lys | Asp | Gln | His |
|   | Met | Asp | OH  |     |     |     |     |     |     |     |     |     |     |     |     |

As has been discussed in the literature articles previously identified, sufficient homology exists between species so that the S-peptide or S-proteins derived from ribonucleases from these species should be capable of use as components of catalytic polypeptide pairs in accordance with the present invention.

Further, as discussed above, the ribonuclease A cleavage product from enzymes other than subtilisin may be employed as the source of polypeptide pairs. It is known that successive pepsin and carboxypeptidase treatments of ribonuclease A give a polypeptide chain shortened by six amino acids (RNase 1-118). (M. C. Lin, *J.Biol.Chem.*, 245 6726, 1970). When this polypeptide was combined with a synthesized tetradecapeptide cor-

| H | Ser | Ser | Ser | Asn | Tyr | Cys | Asn | Gln | Met | Met | Lys | Ser | Arg | Asn | Leu |
|---|-----|-----|-----|-----|-----|-----|-----|-----|-----|-----|-----|-----|-----|-----|-----|
|   | 21  | 22  | 23  | 24  | 25  | 26  | 27  | 28  | 29  | 30  | 31  | 32  | 33  | 34  | 35  |
|   | Thr | Lys | Asp | Arg | Cys | Lys | Pro | Val | Asn | Thr | Phe | Val | His | Glu | Ser |
|   | 36  | 37  | 38  | 39  | 40  | 41  | 42  | 43  | 44  | 45  | 46  | 47  | 48  | 49  | 50  |
|   | Leu | Ala | Asp | Val | Gln | Ala | Val | Cys | Ser | Gln | Lys | Asn | Val | Ala | Cys |
|   | 51  | 52  | 53  | 54  | 55  | 56  | 57  | 58  | 59  | 60  | 61  | 62  | 63  | 64  | 65  |
|   | Lys | Asn | Gly | Gln | Thr | Asn | Cys | Tyr | Gln | Ser | Thy | Ser | Thr | Met | Ser |
|   | 66  | 67  | 68  | 69  | 70  | 71  | 72  | 73  | 74  | 75  | 76  | 77  | 78  | 79  | 80  |
|   | Ile | Thr | Asp | Cys | Arg | Glu | Thr | Gly | Ser | Ser | Lys | Tyr | Pro | Asn | Cys |
|   | 81  | 82  | 83  | 84  | 85  | 86  | 87  | 88  | 89  | 90  | 91  | 92  | 93  | 94  | 95  |
|   | Ala | Tyr | Lys | Thr | Thr | Gln | Ala | Asn | Lys | His | Ile | Ile | Val | Ala | Cys |
|   | 96  | 97  | 98  | 99  | 100 | 101 | 102 | 103 | 104 | 105 | 106 | 107 | 108 | 109 | 110 |
|   | Glu | Gly | Asn | Pro | Tyr | Val | Pro | Val | His | Phe | Asp | Ala | Ser | Val | OH  |
|   | 111 | 112 | 113 | 114 | 115 | 116 | 117 | 118 | 119 | 120 | 121 | 122 | 123 | 124 |     | responding to residues 111 to 124 of the original RNase, essentially the full catalytic activity of RNase was recovered. (M. C. Lin, B. Gutte, S. Moore and R. B. Merrifield, *J.Biol.Chem.*, 245, 5169, 1970; M. C. Lin, B. Gutth, D. G. Caldi, S. Moore and R. B. Merrifield, *J.Biol.Chem.*, 247, 4768, 1972).

Also, as set forth above, enzymes other than ribonuclease A are capable of being enzymatically cleaved to give polypeptide fragments which regain catalytic activity upon non-covalent recombination. Staphylococcal nuclease represents one such enzyme. This polypeptide pair consists of a 42 amino acid polypeptide, designated nuclease T-P$_{(6-48)}$, and a 100 amino acid residue, designated nuclease T-P$_{(49, 50-149)}$. (H. Tamiuchi and C. B. Anfinsen, *J.Biol.Chem.*, 244, 3864, 1969).

An alternate approach to obtaining suitable polypeptide pairs is through mutant microorganisms. For example, as noted above, the Z-deletion mutant of *Escherichia coli* generates a protein designated as the M15 protein which lacks amino acid residues 11 through 41 of the enzyme β-galactosidase. (K. E. Langley, M. R. Villarego, A. V. Fowler, P. J. Zamenhof and I. Zabin *Proceedings National Academy of Science*, 72, 1254 (1975)). The M15 protein recovers essentially full β-galactosidase activity when combined with a small polypeptide fragment (designated CB2) derived from the cyanogen bromide induced cleavage of normal β-galactosidase (K. E. Langley and I. Zabin *Biochem*, 15, 4866 (1976); S. Lin, M. Villarego, I. Zabin *Biochem. Biophys. Research Commun.*, 40, 249 (1970). Also see D. V. Marinkovic, J. N. Marinkovic, *Biochem. J.*, 155, 209 (1976)). Similarly, a small fragment from autoclaved β-galactosidase having molecular weight 7400 also led to recovery of β-galactosidase activity when mixed with the M15 protein (S. L. Morrson and D. Zipser *J. Mol. Biol.*, 50, p. 359, 1970). Other *Escherichia coli* mutant proteins have demonstrated the same phenomenon of recovery of β-galactosidase activity in the presence of chemically derived polypeptide fragments of the normal enzyme. For example, the lacZX90 mutant of *Escherichia coli* provided a protein which recovers β-galactosidase activity in the presence of a 32 amino acid polypeptide designated CNBr 24. The latter is obtained from cyanogen bromide cleavage of β-galactosidase (J. V. Welply, W. Mandeclic, A. V. Fowler, I. Zabin, *Biochem. Biophys. Res. Commun.*, 93, 223 (1980).

It is noteworthy that the association constant for recombination of the CB2 and M15 protein has been estimated to be $1-2 \times 10^9 M^{-1}$ and that antibody to CB2 inhibits recovery of activity with the M15 protein. F. Celada, I. Zabin, *Biochem.*, 18, 404 (1979). Thus, this and related polypeptide pairs can be particularly suitable candidates for use in the immunoassay methodology described herein.

A preferred polypeptide pair is derived from the subtilisin-induced cleavage of ribonuclease A and consists of the S-peptide and S-protein. The structure of the S-peptide and S-protein have been previously described. It should be noted that, in the S-protein, disulfide linkages exist between residues 26-84, 40-95, 58-110, and 65-72, resulting in considerable coiling of the polypeptide. If these disulfide linkages would be cleaved, catalytic activity would likely be lost. These linkages thus help provide a three-dimensional structure for the S-protein which corresponds to that of the original enzyme. This structure provides, in effect, a template for the associating S-peptide which leads to recovery of the active site.

The cleaved enzyme, upon non-covalent recombination, should desirably recover essentially all of the catalytic activity of the original enzyme. At a minimum, sufficient activity should be recovered to convert the substrate to detectable amounts of the reporter molecule at rates substantially greater than those of the medium, or other non-specific medium, induced processes to provide the desired sensitivity and precision. As little catalytic recovery as perhaps 10 or even 5 percent or so may well be satisfactory. Also, the equilibrium constant for association should generally be at least about $10^5$ but no more than about $10^{11} M^{-1}$.

One of the desirable characteristics of the S-peptide, S-protein polypeptide pair is the number and variety of linking sites which the pair provides for bonding with most analytes, without significant diminution of the catalytic activity of the recombined, modified S-peptide, S-protein pair. The epsilonamino groups in the numerous lysine residues in the pair provide numerous sites for convenient covalent coupling of analyte or analyte analogs to either the S-peptide or S-protein. The lysine residues are at positions 1 and 7 in the S-peptide and at positions 31, 37, 41, 61, 66, 91, 98, and 104 in the S-protein. In addition, single alpha-amino groups at the backbone origin of each polypeptide are available for coupling to analytes. Still further, these polypeptide partners include the following groups which might be utilized as linking sites: carboxyl, glutamate, aspartate, histidine and tyrosine.

However, when modifying the S-peptide or S-protein structures for whatever purpose, such as labeling the analyte, the effect on catalytic recovery should be taken into account. For example, considering the amino groups, guanidation or acetylation at all or some of the epsilon-amino groups of the S-peptide should not significantly retard recovery of catalytic activity. Further, preservation of the lysine residue 41 of the S-protein may be crucial for retention of catalytic activity. Bonding of groups such as guanidino, acetyl, trifluoroacetyl, dinitrophenyl and various polyamino acid chains to various lysine residues should not significantly retard catalytic activity of the S-peptide, S-protein, recombined pair except when the epsilon-amino group on lysine 41 is modified. (Richards and Wyckoff reference previously identified, page 678). Thus, use of the S-protein for formation of a useful labeled analyte through bonding of the epsilon-amino lysine groups should be efficacious, provided that the lysine group at position 41 remains unmodified.

Formation of methyl esters of the glutamate residues at positions 2 and 9 or the aspartate residue at position 14 of the S-peptide should provide products with significant retention of catalytic activity. However, it appears that full derivatization of all carboxyl groups must be avoided as this may reduce catalytic activity completely. In the S-protein, modification of one carboxyl group, the carboxyl group corresponding to the aspartate residue at position 53, probably will not reduce catalytic activity.

The histidine groups at position 12 of the S-peptide and at position 119 of the S-protein may be critical for retention of catalytic activity. These histidine groups are believed to participate intimately within the catalytic site as nucleophiles promoting the hydrolytic phosphate-bond cleavage of the natural substrate (RNA) or the various synthetic nucleotide substrates which will be discussed herein. Modifications of the histidine group in either polypeptide fragment may cause complete loss of catalytic activity. Thus, modification of the histidine residues via alkylation or diazonium salt reactions should probably be avoided.

While linking with the analyte may be the principal reason for modification or derivatization of some of the functional groups on the polypeptide label, it should be appreciated that this may be desirable for other reasons. For example, it may be useful to modify the polypeptide label to affect the charge of the resulting labeled analyte. Thus, as one example, guanidation of all or some of the epsilon-amino groups of the S-peptide will provide a less acidic labeled analyte. This may be helpful in providing an approach to altering the competitive equilibriums between antibody and S-protein to enhance assay sensitivity.

Polypeptide pairs, other the S-peptide, S-protein polypeptide pair derived from the cleavage of ribonuclease A, are also suitable for use in the present invention. Such pairs will recombine in such a manner as to provide the desired catalytic activity. Particularly, it has been found that certain polypeptides will so recombine with the S-protein. Such pairs include, for example, the polypeptides consisting of residues 1 through 13 and 2 through 13 of the S-peptide. Also, the following polyamino acids should be useful polypeptide partners for the S-protein: 1 or 2–14; 1 or 2–15; 1 or 2–16; 1 or 2–17; 1 or 2–18; 1 or 2–19, and 1 or 2–20 (F. M. Finn and K. Hofmann, *Accounts of Chem. Research*, 6, 170 (1973)).

Further, there are a wide range of synthetic S-peptide analogs which may be utilized for the formation of labeled analyte. Such analogs should exhibit catalytic activity in the presence of the S-protein and provide functional groups suitable for coupling to the analyte. Thus, in view of the literature, certain residues along the S-peptide chain should be capable of being replaced with other amino acids and still provide the desired catalytic activity in the presence of the S-protein. For example, a lysine or ornithine residue should be capable of being substituted for arginine at position 10 (A. Rochi, F. Marchiori, L. Maroder, A. Fontana, and E. Scoffone, *Gazz.Chim.Ital.*, 96, 1537, 1966). The 10-ornithine substituted peptide should also be capable of being substituted at positions 4 and 5 by a serine residue for the alanine residue at these positions. (L. Maroder, A. Rochi, F. Marchiori, A. Fontana, and E. Scoffone, *J.Amer.Chem.Soc.*, 91, 3921, 1961). Similarly, a tyrosine residue should be capable of being substituted for phenyl alanine at position 8 in the same ornithine substituted polyamino acid. (R. Rochi, L. Maroder, F. Marchiori, E. Ferrarese, and E. Scoffone, *J.Amer.Chem.Soc.*, 90, 5885, 1968; F. Marchiori, R. Rochi, L. Maroder, and E. Scaffone, *Gazz.Chim.Ital.* 96, 1549, 1966).

With respect to the preferred polypeptide partners (viz. - S-peptide and S-protein), incubation of an equimolar mixture has been found to lead to essentially full recovery of the enzymatic activity of the native protein, ribonuclease A, towards a variety of substances such as for example, ribonucleic acid (RNA) and cytidine 2', 3'-phosphate diester. Further, it has been found that the labeled analyte complex resulting from the recombination of the S-peptide labeled analyte with its polypeptide partner, S-protein, recovers the catalytic activity of the S-peptide, S-protein complex towards the substrate mononucleotide 3'-phosphodiester.

Labeled Analyte

Functionally, the labeled analytes suitable for use in the present invention are characterized by their ability to provide catalytic activity when exposed to a polypeptide partner, and by their ability to combine with specific antibody or receptor protein specific for the analyte, with concomitant loss of catalytic activity when so bound. Also, it is desirable for such labeled analytes to exhibit good stability towards a variety of reagents under various reaction conditions such as would be encountered in preparation and use, and be readily purified.

Chemically, the labeled analytes of the present invention comprise, in general, an analyte chemically linked with one of the polypeptide partners. In some instances, the analyte or the polypeptide partner, or both, contain suitable functional groups for carrying out the linking. In other situations, more typically for the analyte, it may be desirable or necessary to form an analog by incorporating one or more functional groups into the molecule. Indeed, to facilitate formation of the labeled analyte or to insure retention of the desired catalytic activity, it may be desirable or essential to form analogs to carry out the linking even where functional groups are present. Further, it may be appropriate in some situations to utilize a linking group to spatially separate and link together the analyte and polypeptide partner. It should also be noted that the polypeptide labels used in this invention, e.g. - S-peptide, tend to be smaller molecules than enzyme labels so that characterization and precise structural determination are facilitated. Lastly, it may be desired for certain assays to link more than one analyte molecule to a single polypeptide label molecule while in other assays linking more than one polypeptide label molecule to a single analyte molecule might be preferable.

In general, the polypeptide labeled analytes of this invention may be represented by the formula:

$$A_m\text{-}X_n\text{-}Z_o\text{-}Y_n\text{-}[PP_1]_p$$

wherein:

A is the analyte analog resulting from linking;

X is the moiety which is linked to A and either Z or Y;

Z is a bridging group which, if present, is linked to X and Y;

Y is the moiety linked to $PP_1$ and either Z or X;

$PP_1$ is a polypeptide partner;

m, n and p are integers of from 1 to about 8, and o is zero or an integer of from 1 to about 8 which in the normal case will have the same value as n.

When more than one analyte molecule is linked to a single polypeptide molecule, the labeled analyte may be represented by the formula:

$$[A\text{-}X\text{-}(Z)_o\text{-}Y]_n\text{-}PP_1$$

wherein A, X, Z, Y and $PP_1$ have the same meanings as in the prior formula, o is either zero or one and n is an integer greater than 1. Generally, n will not exceed a value greater than about 8 and will, more usually, be no greater than 3.

If more than one polypeptide molecule is linked to a single analyte molecule, the formula becomes:

$$A\text{-}[X\text{-}(Z_o)\text{-}Y\text{-}PP_1]_n$$

wherein A, X, Z, Y, $PP_1$, n and o have the meanings described in the immediately prior formula (viz. - where more than one analyte molecule is linked to a single polypeptide molecule).

In forming the labeled analytes of this invention, the smallest value of m, n and p will generally provide preservation of both immunoreactivity and catalytic activity recovery, owing to minimum disruption of the corresponding structural determinants of both the analyte and the label. On the other hand, higher values may prove advantageous, provided that either immunoreactivity or antibody-based inhibition of catalytic recovery is enhanced. The optimum value may be readily determined experimentally for the specific assay involved.

Many analytes incorporate one or more functional groups at suitable positions in the molecule to allow for linking. However, for some analytes, the introduction of functional groups such as, for example, amino, carboxyl, hydroxyl and thiol to the analyte molecule may be required. Similarly, the polypeptide label will, in general, incorporate, as one example, numerous free amino groups suitable for linking to provide the moiety, Y. Thus, when S-peptide is used as the label, three amino groups are present; and one or all of these may be utilized for linking without loss of catalytic activity in the presence of S-protein. In certain situations, however, it may be useful to use other polypeptide functional groups which are frequently encountered, including the carboxyl, hydroxyl and thiol functional groups. For example, such other functional groups may be desirably used to provide advantageous results insofar as various reaction equilibria are concerned, e.g. - $K_2$ and $K_3$.

The moieties X and Y which are preferred according to the nature of functional group utilized for the analyte and polypeptide label and which may be identical, are set forth below:

| EXAMPLES OF LINKING GROUPS | |
|---|---|
| Functionality on A, $PP_1$ | X, Y |
| $NH_2$ | —NH—C(=O)— |
| | —NH—C(=O)—NH— |
| | —NH—C(=S)—NH— |
| \>NH | \>N—CH$_2$— |
| $CO_2H$ | —C(=O)—O— |
| | —C(=O)—NH |
| OH | O—C(=O)— |
| | O—C(=O)—NH |
| SH | O—CH$_2$— |
| | —S—C(=O)— |

-continued

| EXAMPLES OF LINKING GROUPS | |
|---|---|
| Functionality on A, $PP_1$ | X, Y |
| | —S—C(=O)—NH |
| | —S—C(=S)—NH |
| | —S—(succinimide N—) |
| —R—N≡N$^+$ | —NH—C(=O)—C$_6$H$_4$—N=N—C$_6$H$_4$—OH |

In the last example set forth, a diazonium salt may be formed by reaction of the amino group with acidic sodium nitrite or other suitable reagent, followed by reaction with a hydroxylphenyl moiety such as tyrosyl or the like. The hydroxyl group may be located at the para position as well as the ortho position shown, and the remaining bond (shown at the para position) may be located at any other position on the ring.

The group Z bridges the linking groups X and Y. It may not be necessary in all instances as the particular functional groups for the analyte and polypeptide label may in some cases be suitably linked together without the need for the interposition of a bridging group. Generally, the bridging group Z, when present, can be an alkylene group of from 1 to 10 carbon atoms, an alkylene group of from 1 to about 10 carbon atoms, a cycloalkylene group of from about 4 to about 10 carbon atoms, an oxoalkylene group of from about 2 to about 10 carbon atoms and an arylene group of from 6 to about 10 carbon atoms.

The function of the bridging group Z is to provide another structural parameter whereby immunoreactivity, recovery of catalytic activity and inhibition of catalytic activity by anti-analyte antibody may be optimized. Thus, the bridging group provides, in a functional sense, a chemically inert spacing arm to separate the analyte and the label. In addition, as will be discussed hereinafter, this facilitates preparation when bifunctional agents are employed. For example, the use of relatively long chain bridging groups, e.g., - 50 carbon atoms, may satisfy the first two functional requirements but not the third since the label is far removed from the antibody. On the other hand, an extremely short chain bridging group may in some cases lead to loss of immunoreactivity and perhaps catalytic activity.

In accordance with one aspect of this invention, the analyte and polypeptide label may be linked together by using certain bifunctional molecules which incorporate functional groups which have reactivities that are compatible with both the analyte and polypeptide label molecules. Many such bifunctional molecules are known; and suitable examples include glutaraldehyde, bisisothiocyanates, bisisocyanates, isothiocyanato-isocyanates, halogen-isocyanates and isothiocyanates, trimethylsilyl blocked hydroxy isocyanates and the like.

A particularly useful bifunctional molecule is 6-isothiocyanatocaproyl chloride, prepared according to the methods shown in U.S. Pat. No. 4,064,151 (also see H. K. Kricheldorf, *Angew. Chem.*, 87, 517 (1975)). The acid chloride group of this compound is more reactive than the isothiocyanato group and reacts preferentially with an amino or hydroxyl functional group on the analyte molecule. The resulting isothiocyanato derivatized analyte analog is then allowed to react with the free amino group of the polypeptide to form the polypeptide labeled analyte. In the labeled analyte analog so formed:

X will be: —O—C(=O)— or —NH—C(=O)—;
Z will be: —(CH$_2$)$_5$; and
Y will be: —NH—C(=S)—HN—.

Another general method for forming the labeled analyte involves activating a residual functional group on either the analyte or the polypeptide label and then reacting the resultant product with the other component. As one example, a carboxyl group on the polypeptide label can be converted to a derivative which is more reactive with a functional group on the gentamicin molecule, and the resulting product then condensed with gentamiacin to form the labeled analyte. On the other hand, to label dilantin, a carboxyl group introduced on the dilantin molecule may be derivatized; and the resulting product is then reacted with the polypeptide label. Examples of suitable materials for carrying out the derivatization include isobutyrlchloride, N-hydroxy succinimide or a water soluble carbodiimide.

Suggested labeling of various analytes is set forth below.

Anticonvulsant Drugs

The preferred labeled analyte for members of the group of anticonvulsant drugs consisting of dilantin, phenobarbital, primidone and ethosuximide reflect the barbituric acid structure and incorporate a cyclic amide or cyclic lactam functionality within a six or five membered ring as generally shown below:

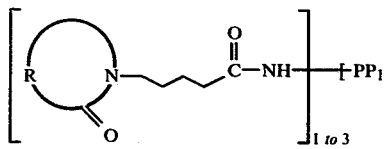

the R group for the various analytes being set forth below:

| Analyte | R |
| --- | --- |
| dilantin | —C(C$_6$H$_5$)$_2$—NH—CO— |
| phenobarbital | —NH—CO—C(C$_2$H$_5$)(C$_6$H$_5$)—CO— |
| ethosuximide | —CH$_2$—C(C$_2$H$_5$)(CH$_3$)—CO— |
| primidone | —C(C$_2$H$_5$)(C$_6$H$_5$)—CO—NH—CH$_2$— |

Specifically, the preferred labeled analyte for dilantin is as follows:

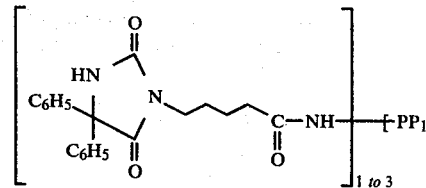

where X is N—CH$_2$, Y is —CO—NH and Z is (CH$_2$)$_3$.

In certain immunoassays, it may be advantageous to retain the free NH-groups in the labeled analyte. In such instances, a derivative of dilantin may be utilized as the labeled analyte. Thus, for example, such a labeled analyte may be provided by introducing an amino group on the phenyl ring through its nitration and reduction, reaction with 6-isothiocyanatocaproyl chloride, and finally reacting the dilantin isothiocyanato derivative with the free amino group of the polypeptide label. The resulting labeled analyte is shown below:

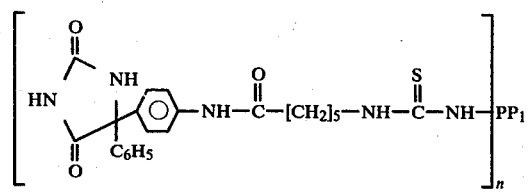

In this case, X is —NH—CO—, Y is —NH—C-S—NH— and Z is —(CH$_2$)$_5$—.

Thyroxine and Triiodothyronine

The preferred labeled analyte for thyroxine is shown below:

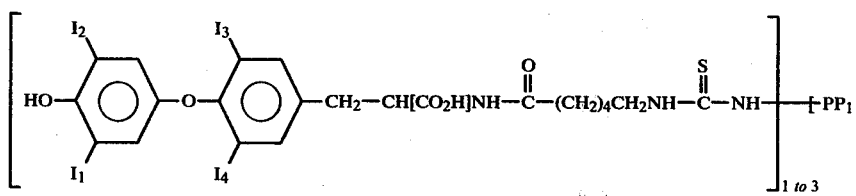

This may be formed by using 6-isothiocyanatocaproyl chloride; and X, Y, and Z are the same as described with the labeled dilantin product using this bifunctional reagent.

Thyroxine labeled analyte may also be obtained directly by condensing thyroxine, in which its amino group is protected by an easily removed blocking group, such as, for example, trifluoroacetyl, with the S-peptide or other polypeptide label. The following thyroxine labeled analyte is ultimately obtained:

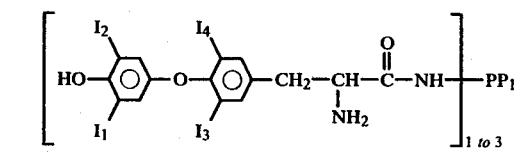

In this case, there is no bridging group and X and Y are —CO—NH.

Triiodothyronine labeled analytes may be similarly formed.

Lidocaine

A labeled analyte suitable for immunoassay of lidocaine may be prepared from the reaction of p-aminolidocaine with 6-isothiocyanatocaproyl chloride, followed by reaction with the polypeptide label. The structure of the resulting product is shown below:

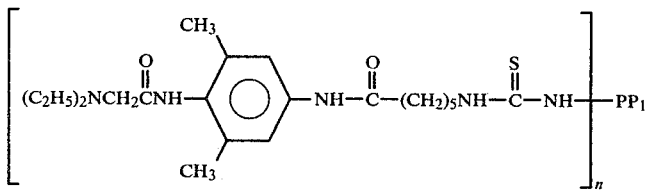

Theophylline

Theophylline and its isomers, caffeine and theobromine, present interference problems because their structures are similar, and because of the presence of caffeine in tea and coffee, and theobromine in cocoa. To insure reactivity with specific theophylline antibody, the theophylline labeled polypeptide should retain the methyl substitution pattern present in theophylline where the 5 and 7 positions remain unsubstituted. The structure for theophylline, caffeine and theobromine are set forth below:

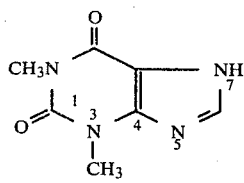

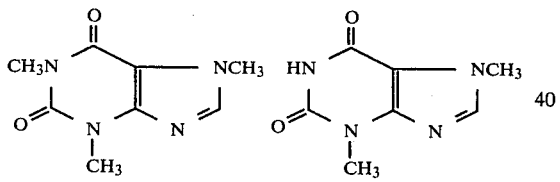

Thus, linkage of the polypeptide label to the theophylline at the methyl group at position 1 should provide a suitable theophylline labeled polypeptide. This results from the fact that the distinctive unsubstituted nitrogen atoms at positions 5 and 7 are retained in the labeled analyte. The antibody used for an assay in this situation should also be derived from an immunogen where the haptenic theophylline group retains unsubstituted nitrogen atoms at positions 5 and 7. This structure is shown below:

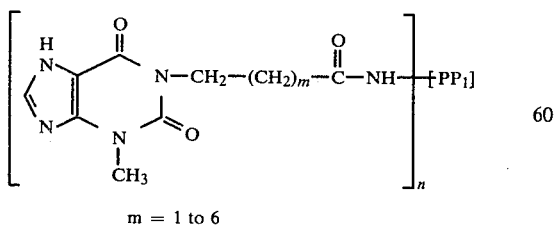

m = 1 to 6

Similarly, derivatives of theophylline at the 3-methyl position and, possibly the 6 position, may be employed for the same reasons as previously discussed.

Amphetamines

Amphetamine labeled analytes may be derived directly from the use of bifunctional coupling agents, such as, for example, 6-isothiocyanatocaproyl chloride. The resulting structure is shown below:

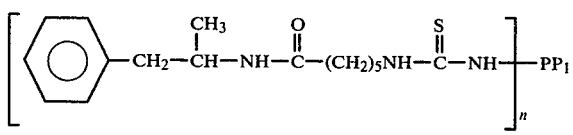

Opiate Alkaloids

Opiate alkaloids of the group consisting of morphine, heroin, and codeine have related structures, as shown below:

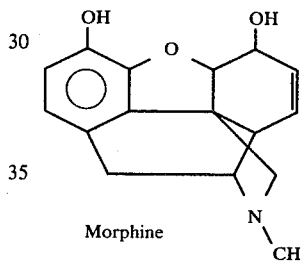
Morphine

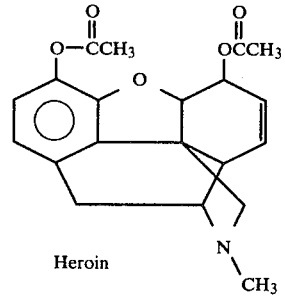
Heroin

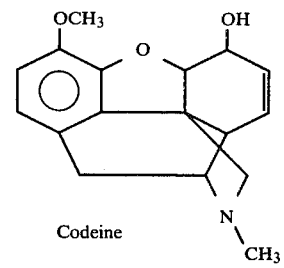
Codeine

Suitable morphine and codeine labeled polypeptides should be provided by the reaction of morphine or codeine with bifunctional agents. For example, reaction of morphine or codeine with 6-isothiocyanatocaproyl chloride provides derivatives which may be linked to a polypeptide label through the resulting free isothiocyanato functionality. Further, derivatives of morphine and codeine may be suitably employed as analyte analogs for labeling with polypeptide. For example, morphine and codeine may be combined with the diazonium salt from p-aminobenzoic acid and the resulting product may then be condensed with the polypeptide label. Similarly, this approach is suggested for heroin since heroin has no free hydroxyl groups.

Antibiotic Aminoglycosides

The antibiotic aminoglycosides, gentamicin, sisomicin, and tobramycin may be labeled with polypeptide by the use of bifunctional agents. Gentamicin, sisomicin and tobramycin all possess a number of free amino groups which provide linking sites for direct coupling to the polypeptide label with such bifunctional agents as, for example, 6-isothiocyanatocaproyl chloride. Gentamicin may also be labeled by activating free carboxyl groups on the polypeptide by reaction with N-hydroxy succinimide or a water soluble carbodiimide and then condensing with gentamicin to form the labeled analyte.

Cardiac Glycosides

Labeled analytes for the cardiac glycosides digoxin and digitoxin, may be formed with the use of bifunctional agents. Both digoxin and digitoxin have numerous free hydroxyl groups which, upon reaction with the bifunctional agent, 6isothiocyanatocaproyl chloride, provide an isothiocyanato derivative which may be reacted with the free amino groups of the polypeptide to form the labeled analyte. The suggested structure is shown below:

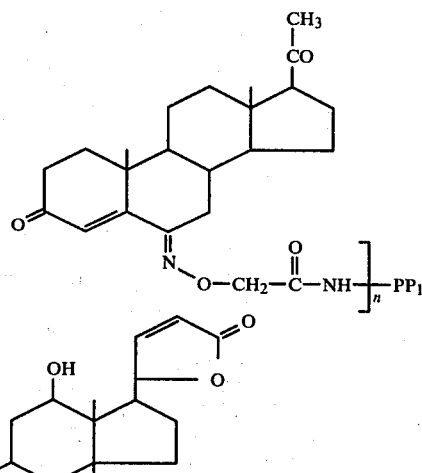

Cortisol

The method described above for digoxin and digitoxin should be equally applicable to cortisol. A suitable structure for cortisol is shown below:

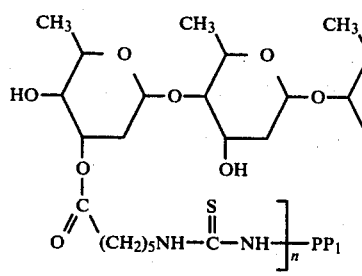

Testosterone

A suggested composition for a polypeptide labeled testosterone is obtained through the same type of synthesis as that shown for cortisol. This composition is shown below:

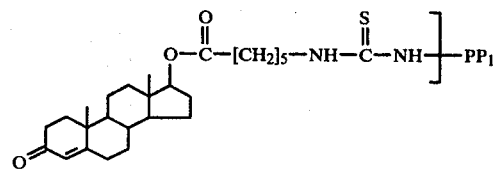

Alternatively, an activated 6-carboxymethyl oxime derivative may be used for coupling testosterone to the polypeptide label.

Progesterone

Progesterone labeled analytes may be provided with a polypeptide label by the reaction of an activated 6-carboxymethyl oxime derivative of progesterone with the polypeptide to give the following composition:

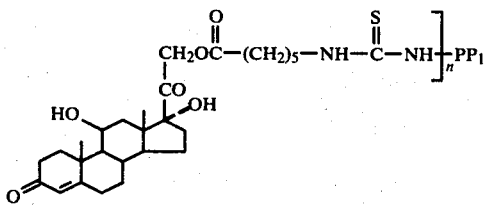

Polyamino Acid Analytes

Labeled polyamino acid analytes, such as, insulin, parathyroid hormones, thyroid stimulating hormone, follicle stimulating hormone, angiotensin II, growth hormone, immunoglobulins and enzymes may be provided by several approaches.

One approach involves the use of bifunctional agents such as glutaraldehyde to link the amino groups of the analyte and the polypeptide label. The resulting general structure is shown below:

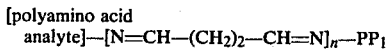

[polyamino acid analyte]—[N=CH—(CH$_2$)$_2$—CH=N]$_n$—PP$_1$

Another approach involves activation of free carboxyl groups with reagents such as isobutyrylchloride or N-hydroxysuccinimide/carbodiimide. The carboxyl groups of either the analyte or the polypeptide label may be activated and followed by the coupling reaction with the second component (viz. - the analyte or label, which ever has not been derivatized). Either of two product configurations may thus be obtained:

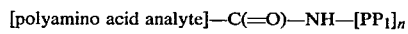

The latter configuration should provide more control of labeled analyte properties, especially with smaller polypeptide labels such as the S-peptide where there are only three amino groups capable of being activated.

A third approach involves the modification of the polypeptide label with a bifunctional group which incorporates maleimide groups. These groups can then undergo reaction with SH groups of the polyamino acid analyte. The following type of composition is thus obtained:

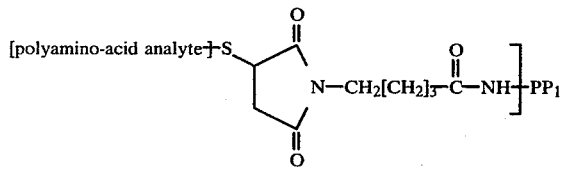

Substrate

Since, as has been stated herein, the substrate is acted upon by the polypeptide pair or, more accurately, the labeled analyte complex, it necessarily follows that the actual nature of the substrate depends on the catalytic properties of the polypeptide pair. Functionally, the substrate should undergo polypeptide pair-induced catalytic release of a chromophoric and/or fluorometric product which may be specifically detected by corresponding spectrophotometers or fluorometers. Further, it is desirable that the catalytic conversion of substrate to producet (i.e.—reporter molecule) be rapid enough so that the appearance of product can be monitored kinetically over a relatively short period of time, for example, less than one hour. This requires, in general, that a chromogenic substrate be used for analytes present in concentrations greater than $10^{-9}$ M, while a fluorogenic substrate be utilized for analyte concentrations of less than $10^{-9}$ M.

It is also desirable that the rate of appearance of the reporter molecule be a linear, or nearly linear, function of time over the measurement period. It is further desirable that the substrate be capable of being readily prepared and that it have sufficient stability to allow strorage in a buffer medium or in lyophilized form for a minimum of one week, and preferably for at least three months.

In the assay, the substrate concentration should be high enough so that substrate depletion during the course of the assay does not occur. Stated another way, the rate of turnover of the substrate should be independent of substrate concentration during the time period of the assay. In general, concentrations of substrate between about $10_{-4}$ M to about $10^{-2}$ M should be acceptable.

For use with the preferred polypeptide pair, it is preferred that substrates be utilized which are enzymatically converted to reporter molecule by ribonuclease A. For the polypeptide pair derived from the enzyme staphylococcal nuclease, suitable substrates are those which are converted to a reporter molecule by the native enzyme. For example, the paranitrophenyl ester derivatives of deoxythymidine 5'-phosphate may be utilized. P. Cuatrecasas, M. Wilchek, and C. B. Anfinsen, "The Action of Staphyloccal Nuclease on Synthetic Substrates", *Synthetic Substrates of Staphyloccas Nuclease*, Vol. 8, No. 6, pp. 2277-83, June, 1969. For polypeptide pairs related to β-galactoside, a suitable substrate in o-nitrophenyl β-galactoside which is commercially available.

However, for the S-peptide and S-protein polypeptide pair, the structure generally preferred for a substrate is as follows:

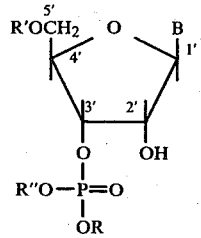

wherein: B is a nucleotide base such as, for example, pyrimidine analogs such as uracil, capable of assisting in catalytic or enzymatic hydorlysis of the phosphate ester at the 3' position;

R is a moiety selected from the group consisting of umbelliferonyl, 4-methylumbelliferonyl, 3-flavonyl, o-nitrophenyl, m-nitrophenyl, p-nitrophenyl, dinitrophenyl, cyanophenyl, acylphenyl, carboxyphenyl, phenylsulfonate, phenylsulfonyl and phenylsulfoxide;

R' is a moiety selected from the group consisting of hydrogen, alkyl, alkenyl, cycloaklyl, aryl, araalkyl, acyl, oxaalykyl, thioalkyl, oxacycloalkyl and thiocycloalkyl;

R" is hydrogen or a cation selected from the group consisting of calcium barium, lithium, sodium, ammonium, substituted ammonium, and pyridinium.

There are, generally, several methods by which the preferred substrates may be prepared. One method involves the synthesis of 2'-O-tetrahydropyranyl-5'-O-acetyl-uridylic acid as an intermediate which is subsequently condensed with the free alcoholic fluorophore or chromophore; whereas a second method involves the use of t-butyldimethylsilyl blocking groups and is based on the direct silylation of uridine to form the 2', 5'-blocked uridine. The preferred substrates and manner of making them are described more fully in the previously identified co-pending applications filed on even date herewith.

Also, a suitable substrate may further consist of the above structure wherein R is naphthyl. In this case, the free naphthyl obtained upon catalytic hydrolysis of the substrate is detected by reaction with a diazonium salt, the salt being derived from sulfanilic acid. The final product is an azo dye having intense absorption in the visible range at 500 nanometers. This substrate has been found useful for the colorimetric assay of thyroxine.

While purine bases, such as, for example, adenosine and guanosine, will not provide suitable substrates (when substituted for the pyrimidine base in the above structure) for monitoring the catalytic activity of ribonuclease A or related polypeptide pairs, substrates incorporating purine bases should prove useful when other polypeptide pairs are employed. For example, the latter would be useful for monitoring the activity of microorganism-derived ribonuclease $T_2$ which has activity for purine bases or polypeptide partners derived from $T_2$.

Substrates useful for the particular catalytic activity provided by other polypeptide pairs are known. Further, in view of existing literature, suitable substrates for the enzymatic activity expressed by a particular polypeptide pair may be designed.

The preferred substrates described herein can undergo, in certain environments, medium-induced hydrolysis and this provides undesirable background conversion of the substrate to reporter molecule. This medium-induced hydrolysis reaction can occur in some substrates rapidly at high pH, i.e.—about 8 or more, but only very slowly at a lower pH. This may be of concern when long term storage (i.e.—more than one day or so) of these substrates is contemplated. Storage at a low pH and at relatively low temperatures will minimize hydrolysis.

However, medium-induced hydrolysis can be essentially eliminated by derivatizing the 2' substitutent with an easily removable blocking group. Thus, when long term storage is contemplated, the substrate is represented by the following formula:

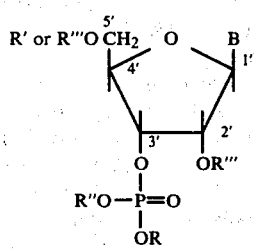

wherein:
R''' is a blocking group, and
R, R', R'' and B are the same moieties as described in conjunction with the previous formula for the substrate.

Suitable 2'-blocking groups should meet the following criteria: (1) readily introduced without affecting the other key functionalities, (2) compatible with subsequent synthetic steps, and more particularly, should minimize or eliminate undesired side reactions in such steps, (3) sufficiently stable to allow long-term storage without any adverse deleterious affects and (4) easily removed without disruption of the phosphodiester bond. These criteria, and especially the last one, are most readily met by use of a blocking group capable of being introduced and removed by acid-catalyzed reactions.

Thus, suitable blocking groups R''' include silyl, oxaalkyl, thioalkyl, oxacycloalkyl and thioalkyl. More particularly, tetrahydropyranyl, 4-methoxytetrahydropyranyl, 1-ethoxyethyl and t-butyldimethsilyl may be used. Use of the first three blocking groups, that is, tetrahydropyranyl, 4-methoxytetrahydropyranyl and 1-ethoxyethyl lead to a ketal structure. These blocking groups are easily removed by weak acids, such as, for example, dilute hydrochloric acid or dilute acetic acid, without disruption of other key functional groups in the substrate molecule. The silyl blocking group is, likewise, easily removed by a reactant such as, for example, tetrabutylammonium fluoride.

The R''' blocking groups may be inserted at the 2' position on the furanoside ring in the course of the synthesis of the substrate itself. However, while not believed essential for providing satisfactory long term storage characteristics, blocking at the 5'-position is necessary during synthesis. Blocking at the 2'- and 5'-positions during synthesis thus prevents premature hydrolysis of synthetic intermediates as well as the occurrence of undesirable reactions at the 2'- and 5'-positions. The blocking groups at the 5'-position need not be removed prior to use of the substrate so the requirement of being capable of being easily removed as is the case with the blocking of the 2'-position is not present.

Other Components

In carrying out an assay, it may be useful to add other components for a variety of reasons. Many such additives are known. Among these may be listed: bacteriostats for improving storage of the reagents; buffers to, for example, improve immunoreactivity or alter catalytic activity; ionic strength agents such as NaCl to enhance immunoreactivity; reagents such as, for example, inhibitors to reduce or eliminate endogenous enzymatic activity; catalytic activity enhancers, and blocking agents for endogenous proteins.

Any of the several additives used in prior immunoassay methodology could be employed in conjunction with the present invention, if desired. However, care should be taken to insure that such additional components do not adversely affect the criteria identified herein for carrying out assays pursuant to this invention. For example, it would not normally be desired to employ a phosphate buffer where the polypeptide pair being utilzed exhibits RNase activity since some inhibition would likely result.

Other General Considerations

It may be useful and, indeed, necessary, in some or all cases to purify the reagents used. For example, purification of a commercial grade polypeptide partner $PP_2$, such as S-protein, to eliminate endogenous enzymatic activity is generally needed. While purification of the peptide label $PP_1$ can be carried out, it will generally be satisfactory to merely purify the resulting labeled analyte. Purification techniques are well known, and chromatographic techniques are suitable. While the substrate can be purified, this has not been found necessary with the preferred substrates described herein.

Lyophilizing some of the assay reagents may be desirable if improved storage requirements are needed. Suitable techniques are known.

It is generally desirable to carry out the assays according to this invention at ambient conditions. However, enhancement or retardation of the raction equilibria, $K_1$, $K_2$ and $K_3$, may result with varying temperatures. This is a further parameter which may be taken into account to provide added flexibility for the methodology of this invention.

The effect of pH on the assay should likewise be considered. For example, in the assay of thyroxine, it has been found that immunoreactivity is decreased as the pH is increased from 5 to about 7. While the naphthyl phosphate substrate described herein may be suitably used at a pH of 5, the preferred umbelliferone-type substrate needs a pH in the range of about 6 to about 8 for useful operation in the colorimetric mode. Sensitivities in pH can perhaps be overcome by changing the charge characteristics of the labeled analyte, as by incorporating more basic groups on the analyte molecule.

Also, the use of a more avid antisera for thyroxine should be helpful. It may also be helpful to modify the linking chemistry (e.g. - the site, type of linking groups).

The principal reagents (viz. - antibody, substrate, labeled analyte and the polypeptide partner) will typically be packaged in kit form for a particular assay together with any additional components needed or desired, such as a set of standard analyte solutions which mimics or covers the anticipated concentration range for the particular analyte. In addition, and depending upon the requirements of the specific substrate being utilized, the following may be included: (1) a deblocking reagent for the substrate if packaged for shipping in blocked form, (2) a buffer for dilutions of reconstituted reagents or for pH adjustment and (3) if required, a dye-forming agent (e.g. - a diazonium salt where the naphthyl phosphate substrate described herein is used). Still further, if necessary to minimize or eliminate potential interferences such as, for example, endogeneous analyte binding protein, pretreatment solutions can be provided.

The various components can be packaged in the kit in solution or lypholized form, depending upon the stability, shipping and other requirements. Each component or reagent can be packaged separately. Alternatively, two or more components may be combined in a single package so long as: (1) the accuracy of the assay is not significantly adversely affected (e.g. - as would occur when the labeled analyte and the polypeptide partner are combined in an environment which would lead to the premature formation of the catalytically active species) and (2) the components will not be degraded in some fashion (e.g. - turnover of the substrate by undue medium-induced hydrolysis).

One mode of combined packaging involves packaging the labeled analyte and the substrate together and combining the antibody and polypeptide partner into a second package. Typically, as when the preferred substrate of the umbelliferone type is used, the substrate in this mode can be in deblocked form, suitably buffered to prevent undue medium-induced hydrolysis. A pH of less than 6 should be used, with a value of about 5 being satisfactory. For a colorimetric detection mode, a separate package of a buffer suitable to provide a pH of 6 or more in the assay is needed in this instance.

An alternative combined packaging mode involves combining the antibody and the polypeptide partner while separately packaging the labeled analyte and substrate. This would be useful to either allow versatility in the protocols that could be employed in the fast analyzers discussed herein or to minimize medium-induced hydrolysis of the substrate, as by packaging this in blocked form. In the latter instance, a separately packaged deblocking agent will be needed. Also, a buffer package for providing an appropriate assay pH may be needed.

A further combined packaging mode involves putting the antibody and substrate together. The labeled analyte and the polypeptide partner would be separately packaged as would be any other additional components.

Regardless of whether the various components are separately packaged in the kit or are combined in some fashion, the auxiliary components described herein (e.g. - bacteriostats) may be added to the appropriate component package.

Although the thrust of the technology described herein is aimed at providing a methodology for homogeneous immunoassay, it should be noted that a heterogenous mode is also possible for the $A\text{-}PP_1/PP_2$ immunoassay label system. This may provide advantages compared to current heterogenous enzyme immunoassay owing to the versatility, ease of preparation, stability, and detection capabilities of $A\text{-}PP_1$-labeled analytes, such as those derived from the S-peptide. Furthermore, special situations may arise where a heterogenous made may be preferred over a homogenous mode. For example, the heterogenous mode offers another option for eliminating serum-based interferences, such as endogenous enzyme activity. Also, unique automated instrumentation may be available for heterogenous immunassays, and the $A\text{-}PP_1/PP_2$ immunoassay label system may allow fuller expression of utility for such systems.

A heterogenous immunoassay protocol involves the following steps:

(1) Incubation of analyte, polypeptide labeled analyte, and anti-analyte antiserum in an appropriate buffer medium;

(2) physical separation of antibody-bound and free polypeptide labeled analyte; and (3) determination of antibody bound-labeled analyte and/or free labeled analyte by adding the corresponding $PP_2$ and substrate and measuring the conversion of substrate to reporter molecule.

Step (2) is readily accomplished by using a solid phase second antibody to the analyte antibody, precipitation of Ab $A\text{-}PP_1$ complexes with agents such as polyethylene glycol, or possibly by chromatography.

Determination of the free $A\text{-}PP_1$ fraction is carried out as in the homogenous mode, whereas determination of the bound fraction may require stripping of the labeled analyte from the solid-phase antibody complexes (since $A\text{-}PP_1$ does not normally recover catalytic activity when bound). This may be accomplished by adding excess $PP_2$ or by use of other agents such as urea, which are commonly used to disassociate antibody complexes. Alternatively, $A\text{-}PP_1$ could be designed so as not to be inhibited by complexing antibody. This may be achieved by using a very large Z group, which, in effect, insulates the $PP_1$ label from the effects of analyte complexation with antibody. Both colorimetric and fluorometric detection modes are possible, as with homogenous immunoassays.

The following Examples are merely illustrative of the present invention and are not intended as a limitation upon the scope thereof. Briefly, Examples I–IV are directed, generally, to the preparation and characterization of thyrozine-S-peptide labeled analyte. Examples V–VIII are directed, generally, to the preparation and characterization of 5, 5-diphenylhydantoin-(dilantin)-S-peptide labeled analyte. Examples IX–X are directed to the preparation and characterization of cortisol-S-peptide labeled analyte. Example XI illustrates the catalytic activity of thyroxine-S-peptide labeled analyte in the presence of S-protein. Examples XII–XVI illustrate the inhibition of catalytic recovery caused by the presence of antibody. Examples XVII–XX are directed, generally to the preparation of standard, or reference, curves. Example XXI is directed to an immunoassay of control and clinical samples. Example XXII is directed to a heterogeneous mode immunoassay. Unless otherwise indicated, the reference to temperatures is to degrees Centigrade.

In the Examples, the following abbreviations are used:

| | |
|---|---|
| a.u. | = absorption unit |
| g | = grams |
| ml | = milliliters |
| mg | = milligrams |
| mmoles | = millimoles |
| ul | = microliter |
| min | = minutes |
| nm | = nanometers |
| % | = percent |
| M | = molar |
| cm | = centimeter |
| na | = nanoamp |
| ma | = milliamp |
| m.a.u. | = milliabsorbance units |
| T. | = temperature |
| ABS. | = absorbance |
| N | = normal |
| ng | = nanograms |
| MV | = millivolts |
| μg | = micrograms |
| TLC | = thin layer chromatography |
| u.v. | = ultraviolet |
| i.r. | = infrared |
| n.m.r. | = nuclear magnetic resonance |

EXAMPLE I

This Example illustrates the preparation of a bifunctional agent, 6-isothiocyanatocaproyl chloride, for use as a linking group in the preparation of labeled analytes.

The bifunctional compound was prepared according to methods similar to those set forth in U.S. Pat. No. 4,130,526 in which bifunctional isocyanates are obtained. The following reactions were utilized:

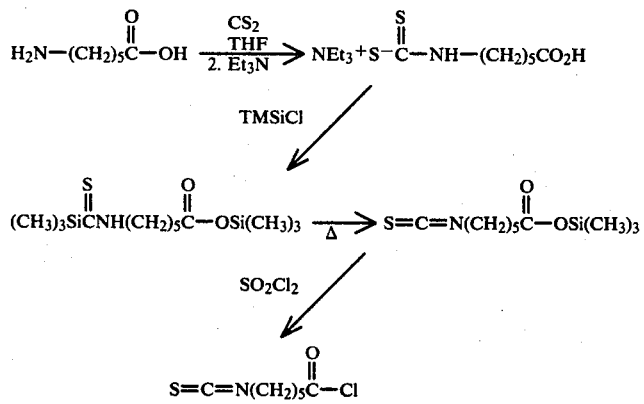

An over-dried and nitrogen-cooled two liter round bottom flask was equipped with a nitrogen inlet, a pressure-equalizing dropping funnel, and mechanical stirrer. A mixture of 6-aminocaproic acid (66.02 g, 0.5 moles) in 500 ml of tetrahydrofuran (dried over Linde 4A Molecular Sieves) was added to the flask. After stirring the mixture for 20 minutes under nitrogen, 240 ml of triethylamine (1.7 moles, dried over Linde 4A molecular sieves) was added with stirring. After stirring for 20 minutes, 36 ml of carbon disulfide (0.6 moles) was added dropwise over a 45 minute period. The reaction mixture was stirred overnight and diluted with 250 ml of tetrahydrofuran. Then 225 ml of trimethylsilyl chloride was added dropwise over a 2.5 hour period. A white precipitate formed. The reaction mixture was gently refluxed with stirring for 7 hours. After cooling, the reaction mixture was filtered in the absence of air. The precipitate was washed with dry tetrahydrofuran, and a red-gold filtrate collected. This tetrahydrofuran solution was concentrated in vacuo at room temperature to remove the solvent. The residue was placed in a 500 ml round bottom flask and dissolved in 250 ml of methylene chloride. Thionyl chloride (70 ml) was then added with stirring over a 20 minute period. After stirring overnight, the solvent was removed on a rotary evaporator to give the crude product. This was distilled twice at 110°-115° (0.2 Torr) to give 31 g of 6-isothiocyanatocaproyl chloride having infrared adsorption bands at 4.6-4.8 u (N=C=S) and at 5.5 u (COCl), and n.m.r. resonances ($CDCl_3$ solvent) at 3.4, 2.8 and 1.5 ppm. in structurally consistent area ratios.

EXAMPLE II

This Example illustrates the reaction of 6-isothiocyanatocaproyl chloride with thyroxine to form a derivative of thyroxine suitable for coupling to the polypeptide label, such as the S-peptide.

One millimole, 776 mg, thyroxine was suspended in 10 ml of methylene chloride. To this was added 0.5 ml of pyridine, and the mixture was cooled in an ice bath. The stirred mixture was then combined with 0.2 ml of 6-isothiocyanatocaproic acid chloride, and stirring was continued overnight. Approximately half of the solvent and other volatiles were removed in a rotary evaporator and the residue was dissolved in a minimal amount of tetrahydrofuran (THF). The THF mixture was transferred into a separatory funnel. The inorganic salts and unreacted materials were removed by extracting the mixture twice with water. The organic layer was dried over anhydrous $Na_2SO_4$. The solvents were removed on a evaporator leaving a residue consisting of the product, N-(6-isothiocyanatocaproyl) thyroxine, which was characterized by thin layer chromatography and elemental analysis.

EXAMPLE III

This Example illustrates the preparation of S-peptide labeled thyroxine formed by the reaction of N-(6-isothiocyanatocaproyl) thyroxine of Example II with the S-peptide.

Commercially obtained S-peptide, (Sigma Lot #99C-8055), 2.94 mg, $1.36 \times 10^{-3}$ mmoles, was dissolved in 1.5 ml of 0.2 M borate buffer of pH 9; and the solution was stirred for 20 minutes at room temperature. To this solution was added 2.09 mg ($9.6 \times 10_{-4}$ mmoles) of N-(6-isothiocyanatocaproyl) thyroxine in 100 μl of dimethyformamide. An additional 50 μl of dimethylformamide was added. The mixture was allowed to stir overnight.

Although thyroxine-S-peptide derivative was found to display both catalytic activity and immunoreactivity when assayed using a 5'-O-acetyl uridine 3'-(4-methylumbelliferone-7-yl phospate) substrate, it was further purified in accordance with Example IV below.

EXAMPLE IV

This Example illustrates the purification of the S-peptide labeled thyroxine formed in Example III.

A Sephadex G-25F column (1×23 cm) was prepared and equilibrated with 0.05 M borate buffer of about pH 9.5 containing 0.02% sodium azide. A portion of the reaction product from Example III (0.5 ml), was applied to the column. Buffer was eluted at a flow rate of 1 ml/min and 1 ml fractions collected. Fractions 14–25 were found to contain the desired conjugate on the basis of an absorbance attributable to thyroxine at 324 nm, catalytic activity in the presence of S-protein and substrate, as shown in Example XI, and immunoreactivity (inhibition in the presence of thyroxine antibody), as shown in Example XII.

Example V–VIII are directed to the preparation of 5,5 diphenylhydantoin (dilantin) S-peptide labeled analyte. In the synthesis described in the Examplles, dilantin is modified to allow coupling to S-peptide via an N-hydroxysuccinimide-induced condensation.

EXAMPLE V

This Example illustrates the preparation of 5,5-diphenylhydantoin 3-(5-valeric acid), C. Cook, J.A. Kepler, H. Dix Christiansen, *Res. Comm. Chem. Path. Pharma.*, 5, 767 (1973), which is coupled to the S-peptide.

Sodium 5,5 diphenylhydantoin (sigma Lot #64C-0027, 1.65 g, 6.01×10$^{-3}$ moles) was added to a 100 ml round bottom flask with dry dimethylformamide (30 ml). The mixture was heated to 60° with stirring, and 1.20 g (6.15×10$^{-3}$ moles) of methyl 5-bromovalerate was added. The reaction mixture was kept at 60° with stirring for 3 hours. It was then poured into 450 ml of 30% saturated ammonium sulfate. A gummy precipitate formed after standing at 5° overnight. The supernatant was filtered, and the residue was triturated with 5 ml of cold methanol. The crude product was filtered and recrystallized from hot methanol. A total yield of 1.41 g (64%) of product, 5,5 diphenylhydantoin 3-(5-valeric acid methyl ester) was obtained.

The 5,5-diphenylhydantoin 3-(5-valeric acid) methyl ester, 0.89 g (2.43 mmole) was refluxed in 50 ml of 0.5N hydrochloric acid in 10% dioxane/H$_2$O for 3 hours. The reaction mixture was colled and stored at 5° overnight. The crude crystalline product was collected by filtration and recrystallized from ethyl acetate/hexane. A total yield of 0.63 g (74%) of product, 5,5 diphenylhydantoin 3-(5-valeric acid), having a melting point of 150–157° (literature mp. 161–163) was obtained. The product was recrystallized again to give purified material having a melting point of 152–153°.

EXAMPLE VI

This Example illustrates the preparation of 5,5-diphenylhydantoin 3-(5-valeric acid N-hydroxysuccinimidyl ester) used in the preparation of the 5,5-diphenyl-hydantoin-S-peptide labeled analyte.

The 5,5-diphenylhydantoin 3-(5-valeric acid) of Example V, 21.36 mg, 5.8×10$^{-2}$ mmoles, was combined with 8 mg (7.0×10$^{-2}$ mmoles) of N-hydroxysuccinimide and 15 mg of dicyclohexylcarbodiimide in 0.66 ml of dry tetrahydrofuran. The mixture was let stand overnight. The reaction mixture was diluted with 10 ml of ethyl acetate and filtered to separate dicyclohexyl urea. The solution was washed twice with 0.5 ml of 0.5 M sodium bicarbonate, once with 0.5 ml of water and once with 0.5 ml of saturated sodium chloride. The solution was dried over anhydrous magnesium sulfate and concentrated on a rotary evaporator. The crystalline residue was recrystallized from methylene chloride/hexane to give 16 mg of product.

EXAMPLE VII

This Example illustrates the preparation of 5,5-diphenylhydantoin (dilantin) S-peptide labeled analyte from the reaction product obtained Example VI.

Commercially obtained S-peptide (Sigma Lot #99C-8055, 0.85 mg. 3.9×10$^{-4}$ mmoles) was dissolved in 0.25 ml of dry dimethylformamide. To the S-peptide dimethylformamide solution, there was added, 0.92 mg., i.e., 20×10$^{-4}$ mmoles. 5,5-diphenylhydantoin 3-(5-valeric acid) N-hydroxysuccinimidyl ester in 0.10 ml of dry dimethyl formamide, followed by the addition of 0.18 mg of N-methylmorpholine in 40 μl of dry dimethylformamide. This reaction mixture was stirred for 1 week at room temperature and then stored at 5°.

Although the dilantin S-peptide labeled analyte was found to display both catalytic activity and immunoreactivity when assayed using a 5'-O-acetyl uridine-3'-(4 methylumbelliferone-7-yl phosphate) substrate, it was further purified in accordance with Example VIII below.

EXAMPLE VIII

This Example illustrates the purification of the 5,5-diphenylhydantoin (dilantin) S-peptide labeled analyte obtained in Example VII.

The dilantin S-peptide labeled analyte was purified by chromatography on a Sephadex G-15 column. Sephadex G15 (20 g) was rehydrated in 150 ml of 0.05 M triethanolamine buffer at about pH 8, containing 0.1% sodium azide, and poured into a 1×48 cm column. The column was equilibrated with buffer, and 100 μl of the labeled analyte prepared as previously described was washed onto the column with small aliquots of buffer. Fractions (1 ml) were collected and monitored for catalytic and immunoreactivity. A 200 μl aliquot of the diluted fraction was combined with 200 μl of sodium acetate buffer or dilantin antibody, 1900 μl of deblocked substrate, 5'-O-acetyl uridine 3'-(4 methylumbelliferone-7-yl phosphate), and 200 μl of an S-protein solution.

The rate of increase of fluorescence was monitored using a commercially available Farrand Mark 1 fluorimeter with excitation set at 325 nm and emission at 440 nm. The following results were obtained for the indicated fractions:

TABLE 1

| Fraction | Rate without Antibody (na/min) | Rate with Antibody (na/min) | % Inhibition (na/min) |
| --- | --- | --- | --- |
| 14 | 0.5 | — | — |
| 15 | 17.5 | 9 | 48.6 |
| 16 | 26.0 | 8 | 69.0 |
| 17 | 36.0 | 6 | 83.0 |
| 18 | 14.5 | 3.5 | 76.0 |
| 19 | 15.0 | 2.5 | 83.0 |
| 20 | 11.0 | 1.5 | 86.0 |
| 21 | 8.5 | 1.5 | 82.0 |
| 22 | 8.0 | 1.0 | 87.0 |
| 23 | 4.5 | — | — |

TABLE 1-continued

| Fraction | Rate without Antibody (na/min) | Rate with Antibody (na/min) | % Inhibition (na/min) |
| --- | --- | --- | --- |
| 24 | 4.5 | — | — |
| 25 | 4.5 | — | — |
| 26 | 6.0 | 1 | 83.0 |
| 28 | 4.0 | — | — |
| 35 | 1.5 | — | — |
| 63 | 1.5 | — | — |

Fractions 15-19 and 20-25 were pooled separately. The pooled fractions 15-19 were subsequently used in the immunoassays described in Examples XV, XVI, and XXI.

EXAMPLE IX

This Example illustrates the preparation of 21-cortisol-(6-isothiocyanatocaproate) used in the preparation of a cortisol-S-peptide labeled analyte.

Triethylamine (0.2 ml) was added using a syringe to a solution of 0.362 g of cortisol in 2 ml of N,N-dimethylformamide. The mixture was stirred in a flask excluded from atmospheric moisture and immersed in an ice-water cooling bath. To the mixture was added 0.229 g of 6-isothiocyanato acid chloride dropwise over a 3 minute period. The reaction was monitored by silica gel thin layer chromatography using 10% methanol in ethyl acetate as an elution solvent. The product had an $R_f$ value of 0.7 compared to an $R_{f\,value\,of}$ 0.5 for cortisol itself. After 3 hours reaction, TLC indicated little or no cortisol. The mixture was then treated with 5 ml of methanol and evaporated to dryness. The residue was crystallized from methanol/ether twice to give 211 mg of white needle (m.p. 105-108). Infrared and n.m.r. data were obtained which was consistent with the structure.

EXAMPLE X

This Example illustrates the preparation of the cortisol-S-peptide labeled analyte from the reaction product obtained in Example IX.

S-peptide, 0.35 mg, was dissolved in 0.3 ml of 0.2 M sodium borate buffer, pH 9.8. To the stirred solution was added 0.5 mg of 21-cortisol-(6-isothiocyanatocaproate) in 0.02 ml of dioxane. An additional 0.075 ml of dioxane was added to make the reaction mixture homogeneous. After stirring for 4 days at room temperature, the mixture was purified through a Sephadex G10 column, 1.0×50 cm, eluting with 0.05 M triethanolamine-HCl1 buffer, pH 8, 0.1% NaCl. Fractions of 2.45 ml were collected. The eluant was monitored using a u.v. detector.

A major band was eluted at Fractions 7, 8 and 9. Assay for catalytic activity in the presence of S-protein and umbelliferone substrate (5'-O-acetyluridine-3'-(4-methylumbelliferone-7-yl phosphate) by the method used in Example VIII showed that these fractions contained about 97% of the eluted S-peptide activity.

The catalytic actvity of these fractions was 65 to 80% inhibited in the presence of cortisol antisera. The ultraviolet spectrum of the labeled analyte had characteristic cortisol absorption at 240 nm; and from this and the absorption epsilon of cortisol itself (11,998), the concentration of labeled analyte was estimated at $7 \times 10^{-5}$ M.

EXAMPLE XI

This Example illustrates the catalytic activity of the thyroxine-S-peptide labeled analyte prepared in Example IV in the presence of the S-protein, and shows the correlation of catalytic activity with concentration of the labeled analyte.

A Union Carbide Corporation Model 500 CentrifiChem ® analyzer was used for monitoring recovered catalytic activity of the thyroxine-S-peptide labeled analyte as a function of its concentration in the presence of the S-protein. Uridine-3'-α-naphthyl phospate/p-diazo sulfanilic acid is used as a substrate/dye combination for monitoring catalytic activity. The following reagents were prepared:

a. Buffer: 0.1 M sodium acetate (pH 5.0)
b. S-protein: $1.5 \times 10^{-5}$ M in sodium acetate buffer;
c. Substrate: 16 mg of freshly deblocked uridine-3'-(α-naphthylphosphate) in 10.7 ml sodium acetate buffer;
d. Dye: 25 mg 1,5-naphthalene disulfonic acid stabilized salt of diazo-p-sulfanilic acid in 1.0 ml of 0.1 N HCl, Lot #031814;
e. Thyroxine-S-peptide labeled analyte: A 1:40 dilution i.e., $1.0 \times 10^{-5}$ M solution of chromatography pool fractions 14-25 purified labeled analyte prepared in Example IV, in sodium acetate buffer.

The CentrifiChem ® analyzer had the following settings: rotor temperature, 30°; filter, 520 nm; test mode, TERM; print out, ABS; ABS, 1.0 u; Blank, Hold; Conc. Factor, 0; Test Code, 0; T, 1 min.

A mixture consisting of 5.55 ml of sodium acetate buffer, 840 μl of substrate, 70 μl of dye, and 140 μl of S-protein was prepared and 400 μl aliquots of the mixture were pipetted into the reagent wells of channels 3 to 12 of the transfer disc of the CentrifiChem ® analyzer. Varying quantities of 5 μl to 40 μl each of thyroxine S-peptide solution were pipetted into the corresponding sample wells of the transfer disc, the total volume in each well being brought to 40 μl with sodium acetate buffer. The loaded disc was placed onto the rotor and spun. Absorbance readings were printed out for each channel at 1 minute intervals. These were converted to rates of formation of the chromophoric product derived from the reaction of naphthol and dye reagent by a least squares linear regression analysis. The data are listed below in Table 2. In general, the correlation coefficients were greater than 0.995 for individual rate measurements.

TABLE 2

| ul thyroxine S-Peptide | rate in absorbance units (a.u.) per minute |
| --- | --- |
| 5 | 0.0086, 0.0080 |
| 10 | 0.0184, 0.0184 |
| 20 | 0.0429, 0.0474 |
| 30 | 0.0697, 0.0721 |
| 40 | 0.0923, 0.0949 |

The concentration of thyroxine-S-peptide could be linearly related to rate of formation of the chromophoric product by the following equation:

rate (a.u./min.)=0.00245 [ul thyroxine-S-peptide]-0.00489 with a correlation coefficient of 0.9995

These data show that the catalytic conversion of substrate is directly related to concentration of labeled analyte and that the rate of this process may be conveniently and precisely determined in a centrifugal fast analyzer as a consequence of the linear relationship between absorbance and time over the measurement period.

Examples XII–XVI show the inhibiting effect of antibody to the analyte on the recovery of catalytic activity of the labeled analyte in the presence of S-protein. Both fluorescent and colorimetric assays are used, as described.

EXAMPLE XII

This Example shows the inhibition of the recovery of catalytic activity of thyroxine S-Peptide by thyroxine antibody using fluorescent assay. The following reagents were prepared:

a. Thyroxine-S-peptide labeled analyte: The product prepared in Example IV was diluted by a factor of 1/2000, using 0.05 M triethanolamine (TEA) buffer, at pH 8;

b. Thyroxine antibody: Antiserum was diluted by a factor 1/200 using TEA buffer;

c. S-protein: Purified commercial material was made up to $2 \times 10^{-5}$ M in TEA buffer;

d. Substrate: freshly deblocked 5'-O-acetyl uridine-3'-(4-methylumbelliferone-7-yl phosphate) in the concentration of about 17 mg of substrate in 50.75 ml of 0.1 M acetate buffer, pH 5.0.

This substrate is catalytically hydrolyzed to give a fluorescent product (4-methylumbelliferone). A Farrand Mark I fluorimeter was used for the rate measurements with the scale set at 0.1. Excitation was at 325 nm and emission was monitored at 440 nm.

Table 3 shows the data obtained after combining the indicated reagents:

TABLE 3

| Solution | Thyroxine-S-Peptide (ul) | S-Protein (ul) | Substrate (ul) | Thyroxine Antibody(ul) | Rate (na/min) |
|---|---|---|---|---|---|
| 1 | 200 | 200 | 1800 | — | 9.8 |
| 2 | 200 | 400 | 1800 | — | 9.0 |
| 3 | 200 | — | 1800 | — | 0 |
| 4 | 200 | 200 | 1800 | 200 | 4.2 |
| 5 | 200 | 200 | 1800 | 400 | 4.0 |

The data for solutions 1 and 2 show that catalytic activity is recovered when the thyroxine-S-peptide is combined with S-protein and that the catalytic activity appears to be saturated with respect to the S-protein concentration. The data for solution 3 shows that catalytic activity is not expressed in the absence of S-protein. The data for solutions 4 and 5 show the inhibited recovery of catalytic activity of the thyroxine-S-peptide due to the presence of thyroxine antibody. The inhibition was 53%.

EXAMPLE XIII

This Example illustrates the inhibition of the recovery of catalytic acitivity of thyroxine S-pepetide by thyroxine antibody using a colorimetric assay.

The reagents used in this Example are the same as those used in Example XI. A mixed solution consisting of 5.55 ml of acetate buffer, 840 μl of substrate, 70 μl of dye, and 140 μl of S-protein was prepared as described in Example XI. Also, the rate of increase of absorbance was monitored using the CentrifiChem ®500 analyzer at the settings described in Example XI. Various concentrations of antibody solution were obtained by diluting the thyroxine antibody with decreasing quantities of acetate buffer.

The mixed solution, 400 μl, was pipetted into the reagent wells of channels 2 through 12 of the analyzer. Decreasing antibody dilutions of 10 μl each were pipetted into sample wells 4 through 12, along with 20 μl of thyroxine S-peptide labeled analyte. Increasing absorbances were monitored at one minute intervals after placing the transfer disc on the instrument rotor and spinning. Table 4 records the results:

TABLE 4

| Channel | Antibody dilution | Rate (a.u./min.) |
|---|---|---|
| 4 | 1:50 | 0.0637 |
| 5 | 1:40 | 0.0622 |
| 6 | 1:30 | 0.0564 |
| 7 | 1:20 | 0.0523 |
| 8 | 1:10 | 0.0490 |
| 9 | 1:6.6 | 0.0471 |
| 10 | 1:5 | 0.0431 |
| 11 | 1:3.3 | 0.0495 |
| 12 | 1:2.5 | 0.0479 |

The data show that the inhibiting effect of antibody plateaued around the 1:10 antibody dilution. A plot of the above data revealed an S-shaped titration curve with 50% inhibition at an antibody dilution somewhat greater than 1:30.

EXAMPLE XIV

This Example illustrates the inhibition of recovery of catalytic activity of dilantin S-peptide by dilantin antibody using a fluorometric assay.

The following reagents were utilized:

a. Dilantin S-peptide labeled analyte: Material prepared as described in Examples V-VIII, which were diluted by a factor of 1/6000 with 0.1M sodium acetate buffer of pH 5;

b. S-protein: Sigman purified commercial material was made up in 0.1M sodium acetate buffer pH 5 at a concentration of $1.47 \times 10^{-6}$M;

c. Dilantin antibody: Antisera was diluted by factor of 1:50 in 0.1M sodium acetate buffer;

d. Substrate: Freshly deblocked 5'-0-acetyl uridine-3'-(4-methylumbelliferone-7-yl phosphate).

A Farrand Mark I fluorometer was used for the rate measurements with the scale set at 0.1. Excitation was at 325 nm and emission was monitored at 440 nm.

To the indicated reagents, 150 μl of S-protein was added; and the solution was incubated for thirty minutes. The data are reported in Table 5:

TABLE 5

| Solution | Dilantin-S-Peptide (ul)* | Buffer (ul) | Substrate (ul) | Dilantin Antibody (ul) | Rate (ma/min) |
|---|---|---|---|---|---|
| 1 | 10 (3) | 300 | 1800 | — | 33.0 |
| 2 | 10 (3) | — | 1800 | 300 | 11.0 |
| 3 | 10 (6) | 300 | 1800 | — | 25.0 |
| 4 | 10 (6) | — | 1800 | 300 | 13.0 |

*The material used in solutions 1 and 2 was the same, but different from the material used in solutions 3 and 4.

The data show the inhibited recovery of catalytic activity of the dilantin-S-peptide due to the presence of dilantin anitbody. For solutions 1 and 2, inhibition is 67%, and for solutions 3 and 4, inhibition is 48%.

EXAMPLE XV

This Example illustrates inhibition of recovery of catalytic activity of dilantin-S-peptide in the presence of S-Protein by dilantin antibody using a colorimetric assay.

In this Example, uridine-3'-(α-naphthylphosphate/p-diazo) sulfanilic acid is used as a substrate/dye combination for monitoring inhibition of catalytic activity with antibody colorimetrically. The following reagents were prepared:

a. Dilantin-S-Peptide labeled analyte: Material prepared in the manner described in Examples V—VIII, of 1:600 dilution using 0.1M sodium acetate buffer of pH 5.0;

b. S-Protein: Sigman purified commercial material made up to $1.53 \times 10^{-6}$ M in 0.1M sodium acetate buffer of pH 5.0;

c. Substrate: Freshly deblocked uridine-3'-(α-naphthylphosphate);

d. Antibody: Dilantin antibody was diluted by a factor of 1:15 using 0.1M sodium acetate buffer.

e. Dye: The stabilized 1,5-naphthalene disulfonic acid salt of p-diazosulfanilic acid (25 mg) was dissolved in 1 ml of 0.1N HCl.

A solution, consisting of 50 μl of dilantin-S-peptide, 20 μl of S-protein, 200 μl of substrate, and 25 μl of dye, was brought up to final volume with 2052 μl of 0.1M sodium acetate buffer of pH 5.0. The solution absorbance at 470 nm was monitored with time, using a Cary Model 118 spectrophotometer in a rate mode. The rate of increase of absorbance (measured in absorbance units, a.u., per minute) was found to be 0.05 a.u./min.

A second solution was made where 111 μl of antibody was substituted for a corresponding volume of sodium acetate buffer. The rate of increase of absorbance was 0.02 a.u./min. corresponding to an inhibition of 60% of the recovery of catalytic activity of the dilantin-S-peptide due to the presence of dilantin antibody.

EXAMPLE XVI

This Example illustrates the inhibition of recovery of catalytic activity of dilantin S-peptide by dilantin antibody in the presence of S-protein using a centrifugal fast analyzer.

This experiment differs from Example XV, owing to the use of uridine-3'-(4-methylumbelliferone-7-yl phosphate) as the colorimetric substrate instead of the naphthyl substrate and a centrifugal fast analyzer (CentrifiChem ®500 ) to monitor rates of increase of absorbance instead of a spectrophotometer. The following reagents were used:

a. Dilantin-S Peptide labeled analyte: Material prepared as described in Examples V–VIII, was used in undiluted form;

b. Antibody: Antiserum diluted by a factor of 1:40 with 0.1M triethanolamine (TEA)-HCl buffer of pH 7.1;

c. S-Protein: Purified material was diluted by a factor of 1:100 with 0.1M TEA-HCl buffer of pH 7.1 to give a final concentration of $1.53 \times 10^{-6}$M;

d. Substrate: 5'-O-acetyl uridine-3'-(4methylumbelliferone-7-yl phosphate) substrate was obtained by deblocking 17 mg of 5'-O-acetyl-2'-O-(tetrahydropyran-2-yl) uridine 3'-(4 methylumbelliferone-7-yl ammonia phosphate) with 750 μl of 0.05N HCl for thirty minutes. The reaction mixture was then buffered by adding 1880 μl of 0.1M sodium acetate of pH 5.0. Just before use, 300 μl of this concentrated substrate was added to 5094 μl of 0.01M TEA-HCl.

The following settings of the CentrifiChem ®500 analyzer were used: Rotor temp, 30°; filter 340 nm; $T_o$, 10 sec; T, 2 min; ABS, 1.0 u; blank, hold; test mode, Term; print out, ABS; conc. factor, 0; test code, 0.

Labeled analyte and antibody or buffer were each pipetted into the sample wells of channels 3 to 6 of the transfer disc of the analyzer followed by the addition of 16.6 μl of 0.025N sodium hydroxide. S-protein and substrate were pipetted into the reagent wells of the same channels of the transfer disc. Channels 0 and 1 were filled with corresponding volumes and an equal volume at TEA buffer. In channel 2, TEA buffer was substituted for dilantin S-peptide and antibody to provide a substrate blank. The disc was placed on the rotor and spun. The absorbances were monitored at two minute intervals and printed out. Rates were obtained by a least squares linear regression analysis of absorbances as a function of time.

Table 6 summarizes the data:

TABLE 6

| Channel | DPH-S Peptide | Antibody | NaOH | TEA | S-Protein | Substrate | Rate(a.u./min) |
|---|---|---|---|---|---|---|---|
| 3 | 33.3 ul | — ul | 16.6 ul | 33.3 ul | 33.3 ul | 300 ul | 0.0208 |
| 4 | 33.3 ul | — ul | 16.6 ul | 33.3 ul | 33.3 ul | 300 ul | 0.0215 |
| 5 | 33.3 ul | 33.3 ul | 16.6 ul | — | 33.3 ul | 300 ul | 0.0149 |
| 6 | 33.3 ul | 33.3 ul | 16.6 ul | — | 33.3 ul | 300 ul | 0.0142 |

The data shows the inhibited recovery of catalytic activity of the dilantin-S-peptide due to the presence of dilantin antibody. The inhibition is 31%.

Examples XI–XVI described above provide the basis for developing standard or reference displacement curves from which unknown analyte concentrations can be determined. The following Examples, Examples XVII–XXI, illustrate standard displacement curves utilizing various colorimetric or fluorometric instrumentation with corresponding substrates.

EXAMPLE XVII

This Example illustrates the generation of a reference displacement curve using thyroxine-S peptide as the labeled analyte and 5'-O-acetyl uridine-3-40 -(4 methylumbelliferone-7-yl phosphate) as a fluorogenic substrate. The following reagents were prepared:

a. Thyroxine-S-Peptide labeled analyte: Material prepared as described in Examples I–IV, was diluted by a factor of 1:2000 in 0.1 M sodium acetate buffer of pH 5.0.

b. Antibody: Antiserum was diluted by a factor of 1:2000 using 0.1 M sodium acetate buffer of pH 5.0;

c. S-Protein: Purified material was brought to $2 \times 10^{-5}$ M using 0.1 M sodium acetate buffer of pH 5.0;

d. Substrate: Seventeen milligrams of 5'-O-acetyl-2'-O-(tetrahydropyran-2-yl) uridine 3'-(4 methylumbelliferone-7-yl ammonium phosphate was stirred in 0.01 HCl for 45 minutes and then extracted with ether. Fifty ml of 0.01 M sodium acetate buffer, of pH 5, was then added to give the substrate solution;

e. Thyroxine antibody standards: Thyroxine solutions were freshly prepared to provide thyroxine concentrations of O ng/ml, 30 ng/ml, 60 ng/ml, 120 ng/ml, and 240 ng/ml in and aqueous medium containing human serum.

Seventy-five microliters of the standard thyroxine solution was pretreated with 20 μl of 0.5 N sodium hydroxide for 10 minutes at room temperature. One hundred microliters of the antibody and 300 μl of thyroxine-S peptide labeled analyte solutions were then added, and the mixture was incubated for 30 minutes at room temperature. A mixture consisting of 1.8 ml of substrate and 100 μl S-protein was then added. After incubating for 5 minutes, the rate of increase of fluorescence was monitored over a 10 minute period.

An Aminco Filter Fluorometer (Model J4-7440) equipped with an automatic 20 sample changer (Model 047-67059) was utilized with excitation at 325 nm and emission at 440 nm. The data points were taken for each sample at times 0, 5, and 10 minutes by an automatic data acquisition system. Table 7 summarizes the results:

TABLE 7

| Tube | Antibody (ul) | Standard (ng/ml, ul) | Thyroxine-S peptide labeled analyte (ul) | Substrate/ protein (ml) | Rate (mv/min) |
|---|---|---|---|---|---|
| 1 | 175 (Buffer) | — | 300 | 1.8 | 15.14 |
| 2 | 175 (Buffer) | — | 300 | 1.8 | 14.76 |
| 3 | 100 | 0,75 | 300 | 1.8 | 12.48 |
| 4 | 100 | 0,75 | 300 | 1.8 | 12.44 |
| 5 | 100 | 30,75 | 300 | 1.8 | 13.00 |
| 6 | 100 | 30,75 | 300 | 1.8 | 13.57 |
| 7 | 100 | 60,75 | 300 | 1.8 | 13.30 |
| 8 | 100 | 60,75 | 300 | 1.8 | 13.40 |
| 9 | 100 | 120,75 | 300 | 1.8 | 13.68 |
| 10 | 100 | 120,75 | 300 | 1.8 | 13.68 |
| 11 | 100 | 240,75 | 300 | 1.8 | 14.15 |
| 12 | 100 | 240,75 | 300 | 1.8 | 14.17 |

The above data show that displacement of bound-labeled analyte occurs as the concentration of thyroxine analyte increases. In order to obtain a displacement curve, the data for duplicate points are averaged; and the % bound fraction (% $B/B_o$) is calculated from the equation:

$$B/B_o \times 100 = \frac{\text{Total Rate} - \text{Rate } B_n}{\text{Total Rate} - \text{Rate } B_o}$$

Where Rate $B_n$ is the rate corresponding to a non-zero standard and Rate $B_o$ is that corresponding to the zero standard solution.

The results are shown in Table 8 below:

TABLE 8

| Point | Std. Conc (ng/ml) | Rate (mv/min) | % $B/B_0$ |
|---|---|---|---|
| Total | — | 14.95 | — |
| $B_0$ | 0 | 12.46 | 100 |
| $B_1$ | 30 | 13.28 | 67 |
| $B_2$ | 60 | 13.35 | 64 |
| $B_3$ | 120 | 13.68 | 51 |
| $B_4$ | 240 | 14.16 | 32 |

The above data can be used to construct a reference displacement curve where rate, % $B/B_o$, or the logit transformation is plotted as a function of standard concentration.

EXAMPLE XVIII

This Example illustrates the generation of a reference displacement curve for determination of unknown concentrations of the analyte thyroxine where a colorimetric substrate is utilized along with a centrifugal fast analyzer.

The following reagents were utilized:

a. Thyroxine S-peptide labeled analyte: Material prepared in the manner described in Examples I–IV was diluted by a factor of 1:400 with 0.1 M sodium acetate buffer of pH 5.0;

b. Antibody: antiserum was diluted by a factor of 1:300 with 0.1 M sodium acetate buffer of pH 5.0;

c. Substrate: Uridine 3'-α-naphthyl phosphate;

S-protein: Sigma plurified commercial material was brought to $2.5 \times 10^{-6}$ M in 0.1 M sodium acetate buffer;

e. Dye: The 1,5-naphthalene disulfonic acid stabilized salt of diazo-p-sulfanilic acid (25 mg.) was dissolved in 1 ml of 0.1 N HCl;

f. Standards: Thyroxine standards at concentrations of 0, 40, 80, 120, and 200 ng/ml were made up in a human serum containing solution.

The following settings were utilized on the Centrifi-Chem® 500 centrifugal fast analyzer: rotor temp, 30°; filter, 520 nm; $T_o$, 10 sec; t, 2 min; ABS 1.0 u; Blank, hold; test mode, Term; Print out, ABS; conc. factor, 0; test code 0.

The standard (20 μl), antibody and polypeptide labeled analyte were pipetted into the sample wells of channels 3 to 14 of the transfer disc. A mixture of 5 μl of the dye, 300 μl of substrate, and 20 μl of S-protein, was pipetted into the corresponding reagent wells along with 10 μl of acetate buffer. The loaded transfer disc was placed on the rotor, and the instrument was spun. Absorbance readings were taken at two minute intervals for a 10 min period, and these were displayed by the CentrifiChem® data acquisition module. These data were converted into rates (a.u./min) by at least squares regression analysis. Table 9 summarizes the data:

TABLE 9

| Channel | Std (ng/ml) | Sodium Acetate Buffer (ul) | Antibody (ul) | Rate (a.u./min) |
|---|---|---|---|---|
| 3 | 0 | 20 | — | 0.0286 |
| 4 | 0 | 20 | — | 0.0304 |
| 5 | 0 | — | 20 | 0.0195 |
| 6 | 0 | — | 20 | 0.0200 |
| 7 | 40 | — | 20 | 0.0208 |
| 8 | 40 | — | 20 | 0.0222 |
| 9 | 80 | — | 20 | 0.0217 |
| 10 | 80 | — | 20 | 0.0218 |
| 11 | 120 | — | 20 | 0.0224 |
| 12 | 120 | — | 20 | 0.0224 |
| 13 | 200 | — | 20 | 0.0230 |
| 14 | 200 | — | 20 | 0.0230 |

A plot of absorbance vs. time for each standard concentration is shown in FIG. 1. The increase in rate, that is, the slope of the curve with increasing standard concentration, illustrates the displacement of thyroxine-S-peptide labeled analyte from the antibody by thyroxine. Also linearity of the data is excellent; correlation coefficients are greater than or equal to 0.9995. Reference displacement curves may be readily obtained from the above data.

Figure 2:
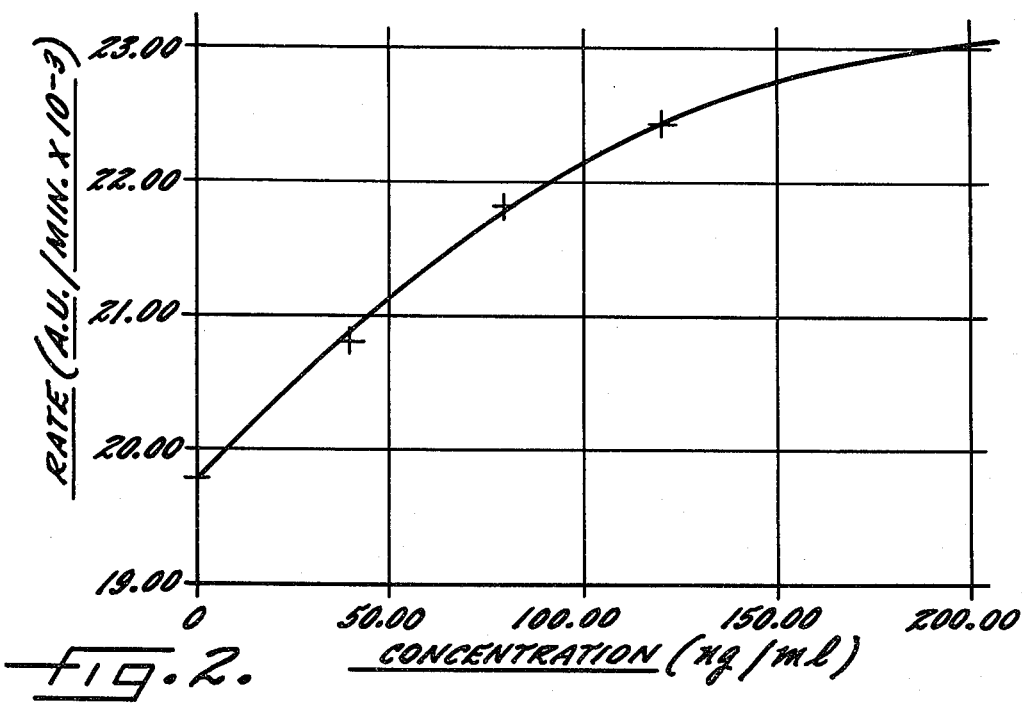
FIG. 2 is a graph of rate of formation of reporter molecule versus concentration for the analyte thyroxine.
Figure 3:
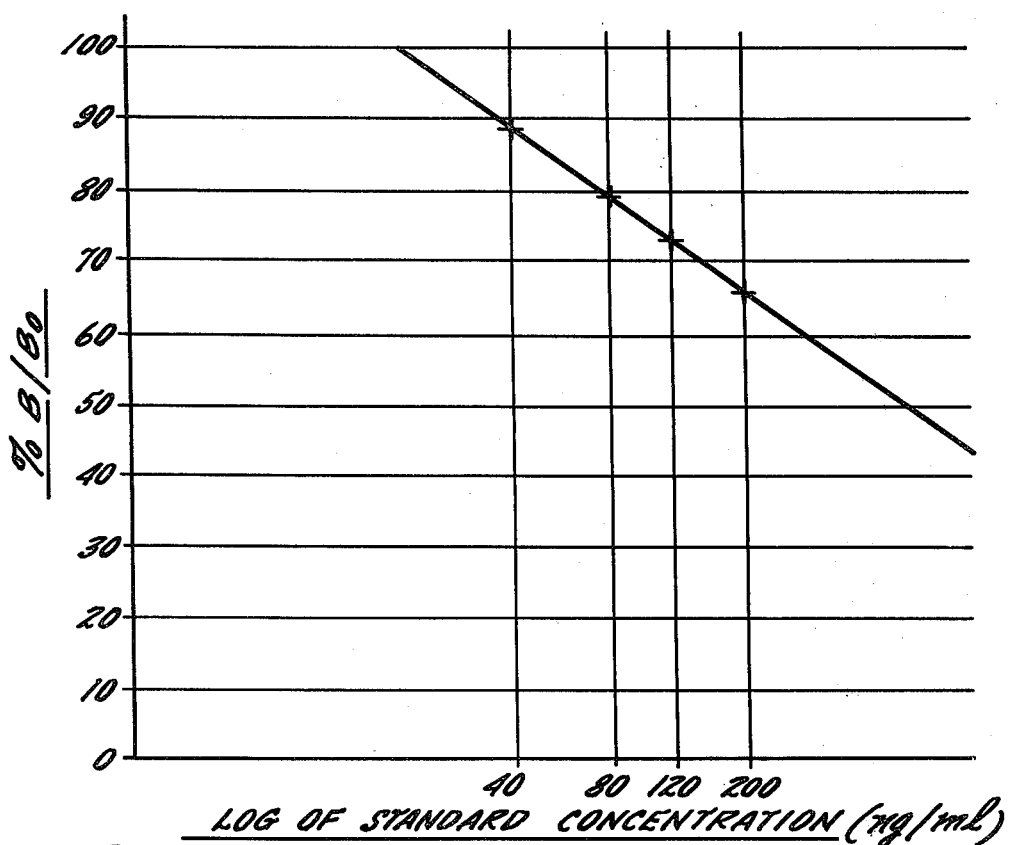
FIG. 3 is a graph of percent antibody bound labeled analyte versus the logarithm of standard concentration for the analyte thyroxine.

FIG. 2 shows a plot of rate v. concentration of standard. The rate data could also be converted to % B/B$_o$ values as described in Example XVII. FIG. 3 shows a plot of % B/B$_o$ vs. the logarithm of the standard concentration.

Although the data in Table 9 reflects a satisfactory response of rate to change in standard concentration, it will generally be more desirable for practical commercial assays to provide a dynamic response substantially greater than that derived from Table 9. Sepcifically, the rate response between the 0 standard and 200 ng/ml standard was 3.5 m.a.u./min.; and a value of about 10.0 m.a.u./min. is preferred.

By appropriate consideration of the concentrations of the various reagents, the dynamic response range can be enhanced.

EXAMPLE XIX

This Example illustrates the interconversion of the thyroxine labeled analyte and S-protein where the S-protein is pipetted into the sample well and the labeled analyte is pipetted into the reagent well, in contrast to the preceding example where the reverse arrangement was used. Additionally, this Example illustrates the formulation of two reagent solutions for direct pipetting into the sample and reagent wells of the transfer disc using an automatic pipetter (Centrifichem ® model P-500 pipetter). Thirdly, this Example illustrates the enhancement of dynamic range in relation to that obtained in Example XVIII by increasing the concentrations of the antibody and S-protein.

The following reagents were utilized:
a. Thyroxine-S-peptide labeled analyte: Material prepared in the manner described in Examples I–IV was diluted by a factor of 1:50 with 0.1 M sodium acetate buffer of pH 5.0;
b. Antibody: Antiserum was diluted by a factor of 1:30 with 0.1 M sodium acetate buffer of pH 5.0;
c. Substrate: Uridine 3'-(α-naphthyl phosphate);
d. S-protein: Sigma purified commercial material was brought to $6 \times 10^{-6}$ M in 0.1 M sodium acetate buffer;
e. Dye: As in Example XVIII.
f. Standards: As in Example XVIII.

A mixture consisting of 500 µl of the substrate, 100 µl of the dye, and 250 µl of the conjugate was prepared. (Reagent A)

A second solution (Reagent B) was prepared by combining 300 µl of the antibody, reagent, 300 µl of the S-protein and 150 µl of 0.1 N. sodium acetate buffer.

The following protocol was utilized for the assay: The standard (20 µl) and 65 µl of de-ionized H$_2$O were delivered to the sample well of the transfer disc by the sample probe of the P-500 pipetter. The reagent B (50 µl) was delivered to the sample well with the second reagent probe of the pipetter. Reagent A (250 µl) was delivered to the reagent well of the transfer disc with the first reagent probe of the pipetter. All three pipetting operations were done simultaneously in one cycle. The transfer disc was then placed on the CentrifiChem ® 400 for analysis. The following settings were utilized for the CentrifiChem ®: temperature, 30°; filter, 520 nm; T$_0$, 10 seconds; T, 2 minutes; Abs, 3.0 u; Blank, hold; test mode, Term; print out, Abs; concentration factor, 0; test code, 0. The following data were obtained:

TABLE 10

| Channel | Std. (ng/ml) | $10^3$ Rate (a.u./min.) |
|---|---|---|
| 2[a] | 0 | 66.9 |
| 3[a] | 0 | 65.9 |
| 4 | 0 | 53.8 |
| 5 | 0 | 54.8 |
| 6 | 40 | 57.8 |
| 7 | 40 | 58.3 |
| 8 | 80 | 60.4 |
| 9 | 80 | 59.5 |
| 10 | 120 | 62.0 |
| 11 | 120 | 64.8 |
| 12 | 200 | 65.3 |

[a] = antibody absent

These data show an enhanced dynamic range compared to that in Table 9. Here, the spread in rate covering the range of standard concentrations of 0–200 (ng/ml) was 12 milliabsorbance units/min. which is about 4 times greater than that achieved in Example XVIII. Furthermore, the data illustrates the formulation of reagent mixtures more suited in certain respects to practical design of a diagnostic kit. Finally, this Example illustrates the use of the automatic pipetter associated with a commercial centrifugal fast analyzer where one pipetting cycle was utilized.

A reference curve can be constructed from the data presented, as is illustrated in Example XVIII.

EXAMPLE XX

This Example illustrates the generation of a reference displacement curve for the dilantin analyte on the CentrifiChem ® 500 centrifugal fast analyzer. A colorimetric substrate, 5'-O-acetyl-uridine-3'-(4-methylumbelliferone-7-yl phosphate), was used.

The following reagents were prepared:
a. Dilantin S-peptide labeled analyte: Material prepared in the manner described in Examples V–VIII in 0.1M triethanolamine (TEA)-HCl buffer was used.
b. Antibody: Anti-dilantin antisera was diluted by a factor of 1/20 with 0.1M TEA-HCl buffer of pH 7.1;
c. Substrate: Seventeen milligrams of 5'-O-acetyl 2'-O-(tetrahydropyran-2-yl) uridine 3'-(4-methylumbelliferone-7-yl ammonium phosphate) was added to 750 µl 0.05N HCl and stirred at room temperature for 30 min. Sodium acetate buffer, (1.880 ml, 0.1M, pH 5.0), was added. Just before use, 300 µl of this solution was combined with 5.094 ml of 0.1M TEA-HCl buffer of pH 7.1;
d. S-protein: Sigma purified commercial material was diluted by a factor of 1:100 with 0.1 M TEA-HCl buffer of pH 7.1 to give a solution having a concentration of $1.53 \times 10^{-6}$M;
e. Dilantin standards: A stock solution of 5,5-diphenylhydantoin sodium salt (Sigma Lot 64C-0027) was made up by dissolving 48 mg in 1 liter of 0.025N sodium hydroxide. This was diluted by a factor of 1:10 with 0.025N sodium hydroxide to give a solution having 4.8 µg/ml. This was further diluted to give standard solutions having concentrations of 19.1, 47.8, 95.8, 143.6, and 191.5 ng/ml.

The CentrifiChem ® 500 centrifugal fast analyzer had the following instrument settings: rotor temp, 30°; filter, 340 nm; T$_o$, 10 sec; T, 1 min; ABS 1.0 u; Blank, hold; test mode, Term; print out, ABS; conc. factor, 0; test code 0.

Antibody, dilantin-S-peptide and 16.6 μl of the standard solution were pipetted into the sample well of channels 3 to 16 of the transfer disc. S-protein and 300 μl of substrate were pipetted into each of the corresponding reagent wells of the transfer disc. The transfer disc was placed on the rotor and spun. Absorbance readings were measured at 1 min intervals for a period of 5 minutes and displayed by the CentrifiChem ® data acquisition module. Catalytic activity rates (a.u./min) were obtained from a least squares regression analysis of absorbances as a function of time.

The data is summarized in Table 11 below:

TABLE 11

| Channel | Std (ng/ml) | TEA-HCl Buffer (ul) | Antibody (ul) | Rate (a.u./min) |
| --- | --- | --- | --- | --- |
| 3 | 0 (0.025N NaOH) | 33.3 | — | 0.0225 |
| 4 | 0 (0.025N NaOH) | 33.3 | — | 0.0230 |
| 5 | 0 (0.025N NaOH) | — | 33.3 | 0.0148 |
| 6 | 0 (0.025N NaOH) | — | 33.3 | 0.0145 |
| 7 | 19.1 | — | 33.3 | 0.0154 |
| 8 | 19.1 | — | 33.3 | 0.0171 |
| 9 | 47.8 | — | 33.3 | 0.0183 |
| 10 | 47.8 | — | 33.3 | 0.0158 |
| 11 | 95.8 | — | 33.3 | 0.0191 |
| 12 | 95.8 | — | 33.3 | 0.0197 |
| 13 | 143.6 | — | 33.3 | 0.0204 |
| 14 | 143.6 | — | 33.3 | 0.0180 |
| 15 | 191.5 | — | 33.3 | 0.0209 |
| 16 | 191.5 | — | 33.3 | 0.0205 |

Figure 4:
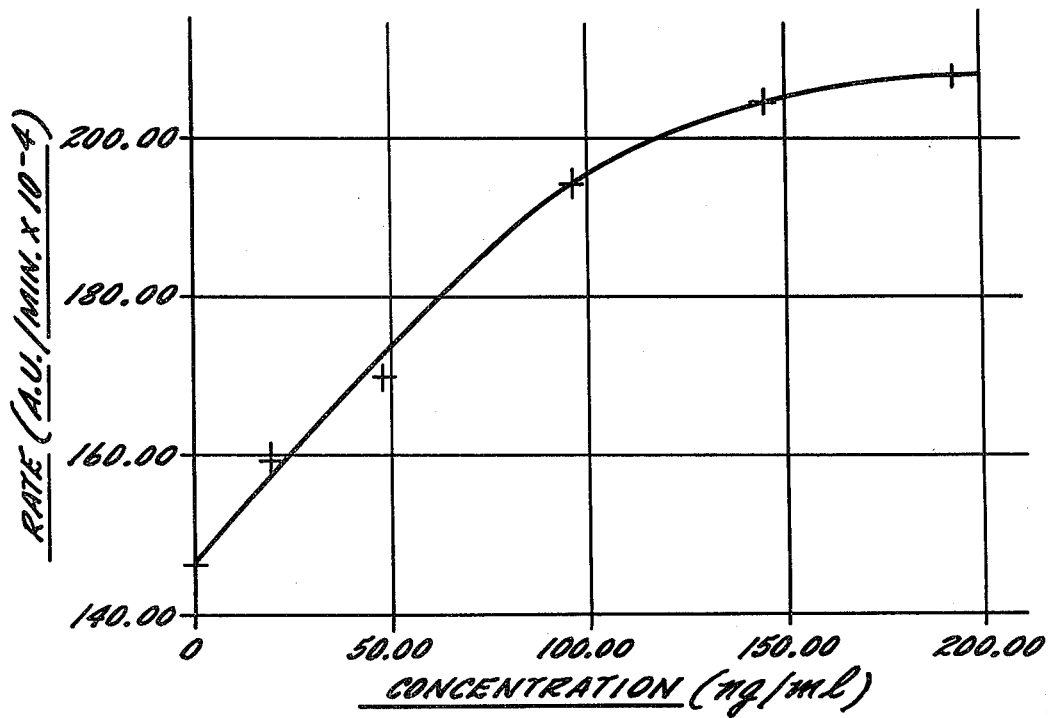
FIG. 4 is a graph of rate of formation of reporter molecule versus concentration for the analyte dilantin.
Figure 5:
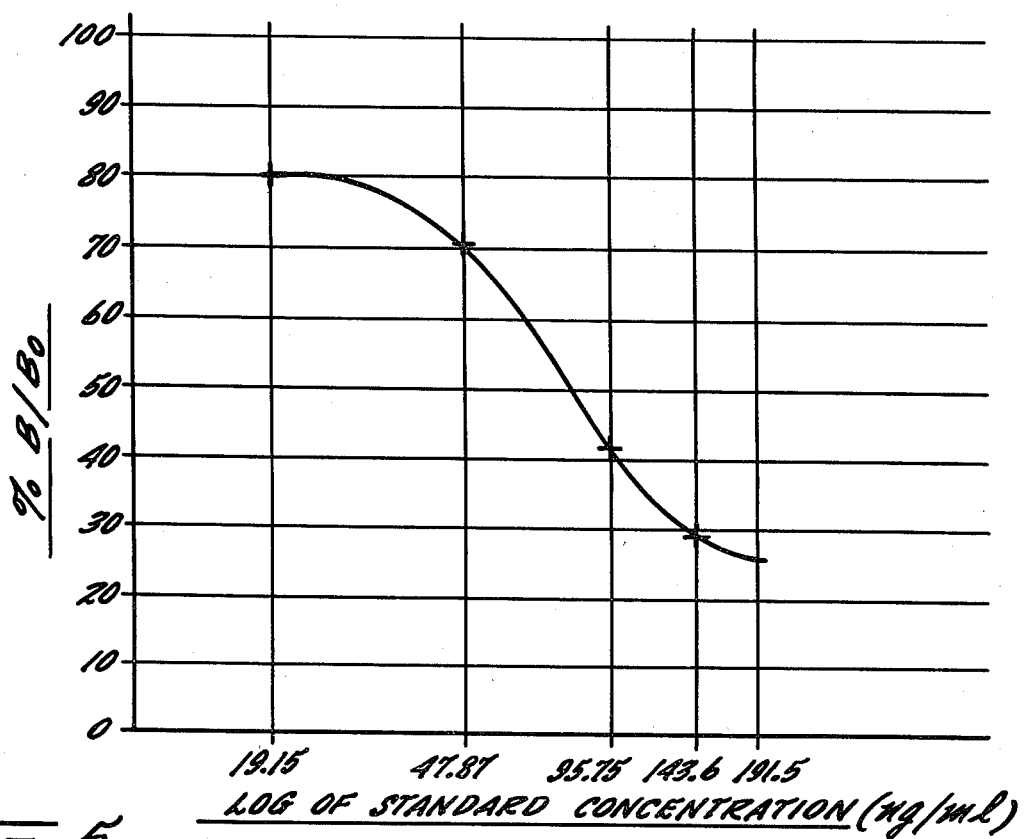
FIG. 5 is a graph of a reference displacement curve of percent antibody bound labeled analyte versus the logarithm of standard concentration for the analyte dilantin.

FIG. 4 shows a plot of rate v. standard dilantin concentration. The percent bound fraction (% $B/B_o$) was also calculated as in Example XVII. FIG. 5 shows the plot of percent bound fraction against standard concentration. The reference displacement curve of FIG. 5 may be linearized by using a logit/log transformation of the data. The linearized reference displacement curve of FIG. 5 is shown in FIG. 6.

Figure 6:
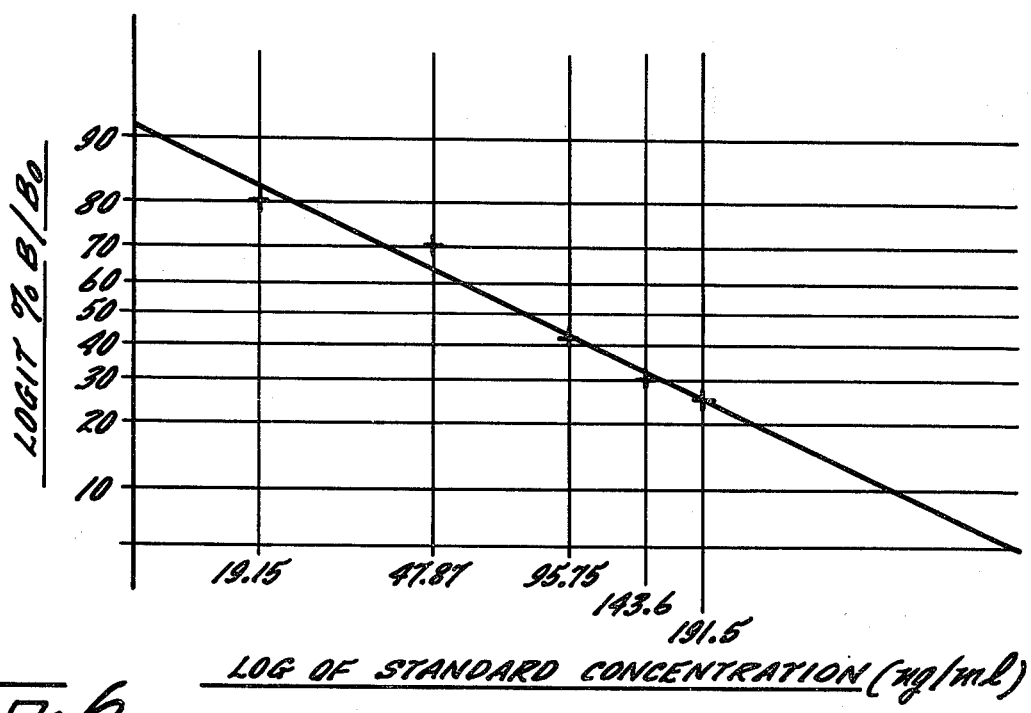
FIG. 6 is a graph of the linearized displacement curve of FIG. 5, obtained by using a logit/log transformation of the data from FIG. 5.

The data displayed in FIGS. 4, 5 and 6 provide a sensitivity over a wide concentration range for dilantin over one order of magnitude. However, this concentration range is less than that normally appearing in human serum. As a consequence, a serum sample would have to be diluted to allow for determination by using the reference displacement curve derived herein.

EXAMPLE XXI

This Example illustrates the design of an assay capable of directly assaying clinical samples, the use of the automatic pipetter (Model P-500) associated with the Centrifichem ® 500 centrifugal fast analyzer, and the use of automatic data reduction.

The following reagents were utilized:

a. Labeled Analyte: Dilantin-S-peptide labeled analyte in 0.1 M triethanolamine (TEA)-HCl buffer, prepared in the manner described in Examples V–VIII was used.

b. Antibody: Anti-dilantin antiserum (150 μl) was diluted with 900 μl of 0.1 M TEA-HCl buffer of pH 7.1;

c. Substrate: 5'-O-acetyl 2'-O-(tetrahydro pyran-2-yl) uridine 3'-(4-methylumbelliferone-7-yl ammonium phosphate) (6.4 mg) was added to 285.2 μl of 0.05 N HCl and stirred at room temperature for 30 minutes. Sodium acetate buffer (714.8 μl, 0.1 M, pH 5.0) was then added;

d. S-protein: A $12.3 \times 10^{-5}$ M solution of Sigma S-protein was made up in 0.1 M TEA-HCl buffer (pH 7.1);

e. Dilantin standards: Solutions of 5,5-diphenylhydantoin sodium salt (Sigma lot 64C-0027) were made up in human serum at concentrations of 2.5, 5.0, 10.0, 20.0 and 30.0 ug/ml.

A mixture of 16 μl S-peptide labeled analyte, 10 μl of human serum albumin, 1430 μl of TEA-HCl buffer, and the substrate solution described in (c.) was prepared (designated Reagent 1). A second mixture consisting of 150 μl of antiserum, 50 μl of S-protein, and 1937.5 μl of TEA buffer was prepared (designated Reagent 2). Using the CentrifiChem ® P-500 automatic pipetter, 4 μl of the appropriate standard solution was simultaneously diluted with 45 μl of deionized H₂O and pipetted into the sample well of transfer disc. At the same time, the pipetter delivered 250 μl of Reagent 1 into the reagent well and 100 μl of Reagent 2 into the sample well. Instrumental parameters for the CentrifiChem ® 500 centrifugal fast analyzer were the same as that for Example XX with the exception that Test Code 29 was used. This provides for automatic data reduction by the microprocessor unit of the CentrifiChem ® 500 instrument.

The following data was obtained:

TABLE 12

| Standard Conc. (μg/ml) | 10³ Response (a.u.) | Calc. Standard Conc. (μg/ml) |
| --- | --- | --- |
| 0 | 215 | 0 |
| 0 | 218 | 0 |
| 2.5 | 230 | 3.1 |
| 2.5 | 231 | 3.3 |
| 5 | 252 | 5.0 |
| 5 | 256 | 5.2 |
| 10 | 358 | 9.6 |
| 10 | 373 | 10.2 |
| 20 | 512 | 23.0 |
| 20 | 494 | 19.1 |
| 30 | 525 | 28.5 |
| 30 | 524 | 27.9 |

The logit-log standard curve stored in the microprocessor unit had a percentage standard deviation of 7.4. In general, the calculated standard concentrations derived from the stored curve satisfactorily agreed with the actual standard concentrations over the analyte concentration range as shown in Table 12.

The above protocol could be used for the direct assay of both control and clinical samples. For example, a clinical sample having a dilantin concentration of 23.4 μg/ml on the basis of gas liquid chromatographic (glc) determination was found to have a concentration of 23.3±.7 μg/ml by duplicate assay as above. Similarly, a clinical sample having a concentration of 2.0 μg/ml by glc was found to have a concentration of 3.1±.1 μg/ml. This illustrates good accuracy and sensitivity over the anticipated analyte range of concentrations in clinical samples. Furthermore, the data indicates the suitability of the assay for automatic pipetting and data reduction and thus takes advantage of the full capability of the centrifugal fast analyzer system utilized. Finally, the data demonstrates the adjustment of concentrations of antibody, S-protein, and dilantin-S-protein labeled analyte to allow for direct determination of clinical samples without prior dilution, beyond that carried out automatically by the P-500 pipetter.

EXAMPLE XXII

This example illustrates the separation of the antibody bound fractions of dilantin analyte and S-peptide labeled dilantin analyte by the use of the double antibody solid phase method, and also shows the dose responsive catalytic activity of the free (unbound) phase. A standard displacement curve is generated from the catalytic activity measurement using 5'-O-acetyluridyl-3'-(4-methylumbelliferone-7-yl) phosphate as a fluorogenic substrate for determination of analyte concentration of the control serum. These data thus exemplify a heterogeneous mode assay.

The following reagents were prepared:
a. Dilantin-S-peptide labeled analyte: Labeled analyte in TEA-HCl buffer was prepared in the manner described in Examples V–VIII; 120 μl was diluted with 2860 μl of TEA-HCl buffer.
b. Antibody: Anti-dilantin antisera (300 μl) was diluted with 1800 μl of TEA-HCl buffer.
c. Solid phase immobilized second antibody: Bio-Rad IMMUNOBEAD ™, Lot 17003, 50 mg was reconstituted with 50 ml of TEA-HCl buffer.
d. Substrate: 5'-O-acetyl-2'-O-(tetrahydropyran-2-yl) uridyl-3'-(4-methylumbelliferone-7-yl) ammonium phosphate, 35 mg, was deblocked with 1.5 ml of 0.025 M HCl for 40 minutes at room temperature and extracted twice with 5 ml of ether. The residual ether was removed by the stream of air and the acidic solution was buffered with acetate buffer to 100 ml.
e. Acetate buffer: Sodium acetate buffer, 0.1 M, pH 5.0.
f. TEA-HCl buffer: Triethanolamine-HCl buffer, 0.05 M, pH 7.5.
g. Dilantin standard: Solution of 5,5-diphenylhydantoin sodium salt was made up in human serum at concentrations of 2.5, 5.0, 10.0, 20.0, 30.0, and 40.0 μg/ml as in Examples XXI.
h. S-protein: Sigma purified solution was diluted 1/20 in acetate buffer.

Appropriate dilantin standards (8 μl each) were pipetted into duplicate test tubes marked as 0 μg, 2.5 μg, 5 μg, 10 μg, 20 μg, 30 μg standards. Antibody aliquots of 100 μl were pipetted into each duplicate tube of standards and the resulting mixtures were vortexed and incubated for 20 minutes at room temperature. Dilantin-S-peptide labeled analyte aliquots of 100 μl each were then pipetted into all tubes. The resulting mixture was incubated for 20 minutes at room temperature.

TEA-HCl buffer (108 μl), and Dilantin-S-peptide labeled analyte (100 μl) were pipetted into duplicate assay tubes labeled total. The resulting mixtures were mixed by vortexing and incubated for 20 minutes at room temperature.

Next a second antibody solution of 500 μl each was pipetted into all tubes except for total assay tubes. TEA-HCl buffer (500 μl) was pipetted into total assay tubes. The resulting mixtures were mixed by vortexing and were incubated for 60 minutes at room temperature. All assay tubes except total were centrifuged for 5 minutes at 3000 rpm at 5°–10° C.

The supernatant (free phase) of each tube was transferred into new tubes marked accordingly. The solid phase was resuspended with 0.5 ml of TEA buffer in each tube and centrifuged as above. The supernatant was decanted off.

Dose responsive catalytic activity was measured as follows:

An aliquot sample (50 μl each) of the free phase and total were assayed respectively with 1.8 ml of substrate and 50 μl of S-protein, measuring the fluorogenic product formation by emission at 440 nm when the mixture was excited at 325 nm, using a Farrand Mark 1 fluorimeter.

The data is summarized in Table 13 below. The raw data were fit by a modified log-logit algorithm where the rates at infinite and 0 standard concentrations are obtained by an iterative procedure. Each data point in the Table represents the mean of duplicate points.

TABLE 13

| Standard Conc. ng/ml | Rate, Mean, na/min. | Calc'ed. Con. from Log-Logit g/ml |
|---|---|---|
| 0 | 8.5 | 0.54 |
| 2.5 | 10.0 | 3.02 |
| 5.0 | 10.5 | 4.00 |
| 10.0 | 14.0 | 11.11 |
| 20.0 | 16.5 | 19.83 |
| 30.0 | 19.0 | 30.86 |
| 40.0 | 20.5 | 40.36 |
| Total | 33.5 | |

The data in the Table leads to an acceptable standard curve over the range of analyte concentrations.

What is claimed is:

1. A non-isotopic competitive binding assay method for determining the amount of an analyte in a sample containing a known analyte in an unknown concentration, which comprises the steps of:
(a) forming a reaction mixture by bringing together in a medium, (1) said sample, (2) polypeptide-labeled analyte, (3) an antibody specific for said analyte, (4) a polypeptide partner capable of non-covalently binding with the polypeptides of the polypeptide-labeled analyte to form a complex having catalytic activity, and (5) a substrate capable of being converted to a reporter molecule by the catalytic activity of said complex, said polypeptide-labeled analyte being capable of competitively binding to said antibody and to said polypeptide partner, said antibody inhibiting the formation of a catalytically active complex in the absence of analyte, the concentrations of said antibody, polypeptide partner and polypeptide-labeled analyte being such as to cause varying amounts of analyte in the sample to be directly related to the conversion of said substrate to said reporter molecule as a function of the catalytic activity of the complex;
(b) measuring the conversion of said substrate to said reporter molecule in said reaction mixture, and
(c) determining the amount of analyte in said sample by comparing the conversion of said substrate to said reporter molecule to conversions of said substrate to reporter molecule obtained with known concentrations of said analyte.

2. The method of claim 1 wherein the complex formed by the non-covalent binding of the polypeptide partner with the polypeptide-labeled analyte exhibits catalytic activity characteristic of a ribonuclease.

3. The method of claim 2 wherein said complex exhibits catalytic activity characteristic of ribonuclease A.

4. The method of claim 2 wherein the polypeptide label for the analyte is S-peptide and the polypeptide partner is S-protein.

5. The method of claim 2 wherein the polypeptide label for the analyte is S-protein and the polypeptide partner is S-peptide.

6. The method of claim 1 wherein at least one of the polypeptide label and the polypeptide partner were obtained by cleaving an enzyme.

7. The method of claim 6 wherein the polypeptide label and the polypeptide partner are cleaved fragments of a parent enzyme.

8. The method of claim 7 wherein the complex formed by the non-covalent binding of the polypeptide partner with the polypeptide-labeled analyte recovers at least 5% of the catalytic activity of said parent enzyme.

9. The method of claim 1 wherein the equilibrium constant for said complex is a value of about $10^5 M^{-1}$ to about $10^{11} M^{-1}$.

10. The method of claim 1 wherein said analyte has a molecular weight of at least about 100 to about $10^6$.

11. The method of claim 1 wherein said analyte is a member selected from the group consisting of a drug or its metabolite, an opiate, narcotic, hormone, steroid, vitamin, polypeptide hormone, tumor associated antigen, immunoglobin, enzyme, industrial pollutant, pesticide or its metabolite, food additive, herbicide or its metabolite, flavoring agent, and food poison.

12. The method of claim 1 wherein said analyte is a member selected from the group consisting of dilantin, ethosuximide, penobarbital, primidone, lidocaine, theophylline, morphine, codeine, heroin, marijuana, gentamicin, tobramycin, methotrexate, digitoxin, thyroxine, testosterone, cortisol, immunoglobulin, triiodothyronine, digoxin, folic acid, angiotensin II, progesterone, prostaglandin F2, estrogens, vitamin $B_{12}$, growth hormone, thyroid stimulating hormone, calcitonin, gastrin, luteinizing hormone, follicle stimulating hormone, glucagon, human chorionic gonadotropin, aldosterone and carcinoembryonic antigen.

13. The method of claim 12 wherein said analyte is dilantin.

14. The method of claim 12 wherein said analyte is thyroxine.

15. The method of claim 12 wherein said analyte is cortisol.

16. The method of claim 1 wherein said analyte is dilantin, the polypeptide label for dilantin is S-peptide and the polypeptide partner is S-protein.

17. The method of claim 1 wherein said analyte is thyroxine, the polypeptide label for thyroxine is S-peptide and the polypeptide partner is S-protein.

18. The method of claim 1 wherein said analyte is cortisol, the polypeptide label for cortisol is S-peptide and the polypeptide partner is S-protein.

19. The method of claim 1 wherein the antibody is present in a concentration sufficient to provide an inhibition of at least about 10%.

20. The method of claim 19 wherein the antibody is present in a concentration sufficient to provide an inhibition of at least about 50%.

21. The method of claim 1 wherein the substrate is present in a concentration such as to provide essentially linear rates over the rate measurement period.

22. The method of claim 1 wherein the substrate is present in a concentration of about $10^{-4}$ to about $10^{-2}$ molar.

23. The method of claim 1 wherein the substrate has the following structural formula:

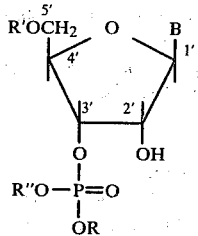

wherein B is a nucleotide base capable of assisting in hydrolysis of the phosphate ester at the 3'-position; R is a moiety selected from the group consisting of umbelliferonyl, 4-methyl umbelliferonyl, 3-flavonyl, o-nitrophenyl, m-nitrophenyl, p-nitrophenyl, dinitrophenyl, cyanophenyl, acylphenyl, carboxyphenyl, phenylsulfonate, phenylsulfonyl and phenylsulfoxide; R' is a moiety selected from the group consisting of hydrogen, alkyl, alkenyl, cycloalkyl, aryl, araalkyl, acyl, oxaalkyl, thioalkyl, oxacycloalkyl and thiocycloalkyl; and R" is hydrogen or a cation selected from the group consisting of calcium, barium, lithium, sodium, ammonium, substituted ammonium and pyridinium.

24. The method of claim 23 wherein B is uracil, R is 4-methylumbelliferonyl, R' is acetyl and R" is a member selected from the group consisting of calcium, pyridinium and sodium.

25. The method of claim 1 wherein said rate is determined spectrophotometrically.

26. The method of claim 1 wherein said rate is determined fluorometrically.

27. A kit for use in carrying out an assay of an analyte, which comprises the following components: (1) a polypeptide-labeled analyte, (2) an antibody specific for the analyte, (3) a polypeptide partner capable of non-covalently binding with the polypeptide of the polypeptide-labeled analyte to form a complex having catalytic activity and (4) a substrate capable of being converted to a reporter molecule by the catalytic activity of the complex wherein the polypeptide-labeled analyte, antibody, polypeptide partner and substrate are present in relative amounts sufficient for the determination of the analyte.

28. The kit of claim 27 which includes a set of standard analyte solutions which covers the anticipated concentration range for the analyte.

29. The kit of claim 27 which includes a buffer for pH adjustment for the assay.

30. The kit of claim 27 wherein each component is separately packaged.

31. The kit of claim 27 wherein the polypeptide-labeled analyte and the substrate are packaged together and the antibody and polypeptide partner are packaged together.

32. The kit of claim 27 wherein the antibody and polypeptide partner are packaged together.

33. The kit of claim 27 wherein the antibody and substrate are packaged together.

34. A non-isotopic competitive binding assay method for carrying out a heterogeneous immunoassay of a sample containing a known analyte present in an unknown concentration which comprises:
(a) forming a reaction mixture by bringing together in a medium (1) said sample, (2) a polypeptide-labeled analyte and (3) an antibody specific for said analyte;

(b) separating the antibody-bound, polypeptide-labeled analyte from the free polypeptide-labeled analyte;
(c) determining the amount of at least one of: (1) the antibody-bound, polypeptide-labeled analyte and (2) the free polypeptide-labeled analyte by adding a polypeptide partner capable of non-covalently binding with the polypeptide of the polypeptide-labeled analyte to form a complex having catalytic activity and a substrate capable of being converted to a reporter molecule by the catalytic activity of said complex, by measuring the conversion of said substrate to reporter molecule, and
(d) determining the amount of analyte in said sample by comparing the conversion of said substrate to reporter molecule to conversions of said substrate to reporter molecule obtained with known concentrations of said analyte.

* * * * *